United States Patent [19]
Yamamoto

[11] Patent Number: 5,903,305
[45] Date of Patent: May 11, 1999

[54] APPARATUS FOR MONITORING WATER QUALITY USING AQUATIC LIVING THING

[75] Inventor: Takahiro Yamamoto, Fukuoka, Japan

[73] Assignee: Anima Electronics Co., Ltd., Fukuoka, Japan

[21] Appl. No.: 08/800,277

[22] Filed: Feb. 13, 1997

[30] Foreign Application Priority Data

Feb. 20, 1996 [JP] Japan .................................. 8-031988

[51] Int. Cl.$^6$ ...................................................... H04N 7/18
[52] U.S. Cl. ............................ 348/61; 210/85; 210/739; 348/89; 702/2; 702/19
[58] Field of Search ................................ 348/61, 86, 89, 348/135, 143, 154, 155; 210/85, 739; 382/110; 702/2, 19; H04N 7/18

[56] References Cited

U.S. PATENT DOCUMENTS

| | | | |
|---|---|---|---|
| 4,626,992 | 12/1986 | Greaves | ........................................ 702/2 |
| 4,744,331 | 5/1988 | Whiffin | ..................................... 119/223 |
| 4,769,776 | 9/1988 | Hiraoka | ...................................... 210/85 |
| 5,505,843 | 4/1996 | Obuchi | ...................................... 210/85 |

*Primary Examiner*—Howard Britton
*Attorney, Agent, or Firm*—Wenderoth, Lind & Ponack, L.L.P.

[57] ABSTRACT

An apparatus for monitoring a water quality by raising an aquatic living thing in a monitoring water tank 1. The monitoring water tank 1 is taken through a camera 12 to be displayed on a television 14. A monitoring area E comprising a plurality of sensor points is set on a television scene through a light pen, and a fish sensing device 13 senses variation of the sensor points in luminance level to continuously detect the moving positions of fish F, F' under observation. A personal computer 15 detects, on the basis of the moving positions of the fish under observation, whether or not each of the fish under observation takes any one of a plurality of abnormal action patterns, and conducts an alarm operation if both the two fish F, F' under observation assume any abnormal action pattern.

6 Claims, 14 Drawing Sheets

APPARATUS FOR MONITORING WATER QUALITY USING AQUATIC LIVING THING

BACKGROUND OF THE INVENTION

1. Field of the Invention

The present invention relates to a water quality monitoring apparatus using aquatic living things for observation of the quality of raw water, where raw water is introduced into a water tank for breeding or raising aquatic living things, and the water tank is taken through a video camera or the like to perform an image or picture analysis of action patterns of the aquatic living things.

2. Description of the Related Art

So far, in a filtration plant or the like there has been provided an apparatus in which aquatic living things such as fish being under observation are raised within a water tank, which continuously receives raw water, to be taken through an industrial television camera or the like so that the taken image is analyzed to grasp the fish's action pattern on the basis of the position at which the fish under observation swims and an alarm is raised if the fish takes an abnormal action. For example, for detection of the position of the fish under observation, the images photographed at a given time interval are stored in an image memory and an image portion corresponding to the fish under observation is recognized by the formation of a differential image between two adjacent images and the position and travelling speed of the fish under observation are detected on the basis of the variation of the position of the center of gravity of the same image portion so that the detected position and travelling speed are compared with the velocity distribution prestored in the normal conditions to detect the abnormality of the water quality (Japanese Patent Publication No. 6-68489).

There is a problem which arises with the above-mentioned prior apparatus, however, in that, since the comparison is made for all the fixed pixels in the image memory, its information quantity is too much to cause the necessity of a long processing time, and when an image other than the water tank comes to within the photographing range of the television camera, the comparison is reluctantly made even for the portions which do not require the comparison, which can make the accurate detection difficult. For these reasons, it is necessary that the water tank is photographed in a state that the entire water tank coincides with the photographing range of the industrial television camera so that all the pixels in the image memory always correspond to the image of the water tank. However, in this case, difficulty is encountered to facilitate the location of the television camera.

In addition, since the above-described prior apparatus is made to compare the travelling speed of the fish under observation with the velocity distribution obtained at the time of the normal conditions, although the detection is possible when the fish takes the typical abnormal action, if the fish takes an action close to an abnormal action, for example if the fish rises to have bait, a judgment to the abnormality can be made in error, and hence it is difficult to accurately decide, through only the comparison with the velocity distribution in the normal conditions, the abnormal action taken for when the water quality is abnormal.

SUMMARY OF THE INVENTION

Accordingly, the present invention has been developed in order to eliminate the above-mentioned problems inherent to the prior apparatus, and it is an object of the present invention to provide water quality monitoring apparatus using aquatic living things, which is capable of setting a monitoring area at an arbitrary position corresponding to a position of a water tank on a television screen to realize accurate and quick image processing and further capable of surely detecting the abnormality of the water quality even if the aquatic living things take various action patterns to be taken in water quality abnormality conditions, so that malfunction is avoidable.

In accordance with the present invention, a water quality monitoring apparatus comprises a monitoring water tank for accommodating raw water and further for raising aquatic living things, a monitoring camera for photographing the aquatic living things within the monitoring water tank, a monitor television for displaying a picture or image taken through the monitoring camera, point setting means for setting a plurality of sensor points within an image of the monitoring water tank displayed on the monitor television, sensing means for recognizing the positions of the respective sensor points and for detecting the occurrence or no occurrence of variation of each of the sensor points in luminance level due to the movements of the aquatic living things at a given time interval and further for, when detecting the variation in the luminance level, outputting position data corresponding to the position of that sensor point, abnormal action pattern detecting means for monitoring action patterns of the aquatic living things on the basis of the position data outputted from the sensing means for a set monitoring time and for deciding whether the action pattern taken for the monitoring time is an abnormal action pattern, and alarm means for raising an alarm on the basis of the decision result by the abnormal action pattern detecting means.

The abnormal action pattern detection means successively accepts the position data outputted from the sensing means and conducts, on the basis of the position data, any one of a first monitoring operation to detect a first abnormal action pattern (for example, a madly running action), a second monitoring operation to detect a second abnormal action pattern (for example, an upward putting-out action), a third monitoring operation to detect a third abnormal action pattern (for example, an evasion action) and a fourth monitoring operation to detect a fourth abnormal action pattern (for example, an active state abnormality such as death). In addition, for the detection of the first to fourth abnormal action patterns the abnormal action pattern detecting means conducts all the first to fourth monitoring operations, and raises an alarm when any monitoring operation detects the abnormal action pattern.

In the first monitoring operation, the moving distance of an aquatic living thing within a monitoring period of time is calculated on the basis of the position data outputted from the sensing means, and when the calculated moving distance exceeds a set distance, a decision is made to that it is an abnormal action pattern, otherwise a decision is made to no abnormality. If the monitoring time and the set distance are appropriate, it is possible to detect the abnormal action patterns, for example, on a madly running action that the aquatic living things swim up and down and in the right and left directions for a short period of time.

In the second monitoring operation, as a first layer there is set a layer with a given depth which exists right under a water surface and extends in horizontal directions within an image of a monitoring water tank, and inside and outside the first layer there are set a plurality of sensor points. The first layer serves as a reference position for detecting, for example, the upward putting-out action that the tip portions of aquatic living things appear on the water surface. Calculation is made to count, as a first number of times of output, the number of outputs of position data indicative of sensor points in the first layer within a monitoring period of time and further to count, as a second number of times of output, the number of outputs of position data representative of sensor points in a section other than the first layer within the monitoring time, and when the second number of times of output exceeds a second set value, a decision is made to no abnormality, and when the first number of times of output exceeds a first set value and the second number of times of output is below the second set value, a decision is made to an abnormal action pattern. If the monitoring time and the first and second set values are appropriate, the abnormal action pattern on the upward putting-out action of the aquatic living thing is detectable.

In the third monitoring operation, as a second layer there is set a layer with a given width which exists within an image of the monitoring water tank and extends in vertical directions in the vicinity of a drainage outlet or scupper, with a plurality of sensor points being set inside and outside the second layer. The second layer acts as a reference position to detect, for example, the evasion action that the aquatic living things evade toward the vicinity of the drainage outlet. Calculation is made to count, as a third number of times of output, the number of outputs of position data indicative of sensor points in the second layer within a monitoring period of time and further to count, as a fourth number of times of output, the number of outputs of position data representative of sensor points in a section other than the second layer, and when the fourth number of times of output exceeds a fourth set value, a decision is made to no abnormality, and when the third number of times of output exceeds a third set value and the fourth number of times of output is below the fourth set value, a decision is made to an abnormal action pattern. If the monitoring time and the third and fourth set values are appropriate, the abnormal action pattern such as the evasion pattern of the aquatic living thing is detectable.

In the fourth monitoring operation, calculation is made for counting the number of times of output of position data within a monitoring period of time and further for the moving speed of aquatic living things. When the number of times of output exceeds a set value (a set number of times) or when the moving speed exceeds a set value (a set speed), a decision is made to no abnormality. On the other hand, in cases where the number of times of output is below the set value and the moving speed is lower than the set value, a decision is made to that the movement of the aquatic living things stops, thus coming to a decision to an abnormal action pattern. If the monitoring time and the set values are appropriate, it is possible to detect the abnormal action pattern on death of the aquatic living thing or the like.

It is also appropriate that the monitoring water tank is divided into a plurality of monitoring sections each for raising aquatic living things. In this instance, the point setting means sets a plurality of sensor points at every monitoring section, while the sensing means checks, at a given time interval and at every monitoring section, whether the luminance level of each of the sensor points varies or not, and further, when detecting the variation in the luminance level, outputs position data corresponding to the position of that sensor point. The abnormal action pattern detecting means monitors the action patterns of the aquatic living things at every monitoring section and raises an alarm through the alarm means only when judging that the aquatic living things take an abnormal action pattern in all the monitoring sections. Even if the abnormal action pattern takes place in one of the monitoring sections, in the case that the aquatic living things assume the normal actions in the other monitoring sections, a decision is made to that this is a problem inherent to the aquatic living thing within the monitoring section undergoing the abnormality detection, for example, because of diseases or the like, but not because of the water quality. With this construction, more certain and accurate water quality monitoring is practicable.

DESCRIPTION OF THE PREFERRED EMBODIMENTS

Figure 1:
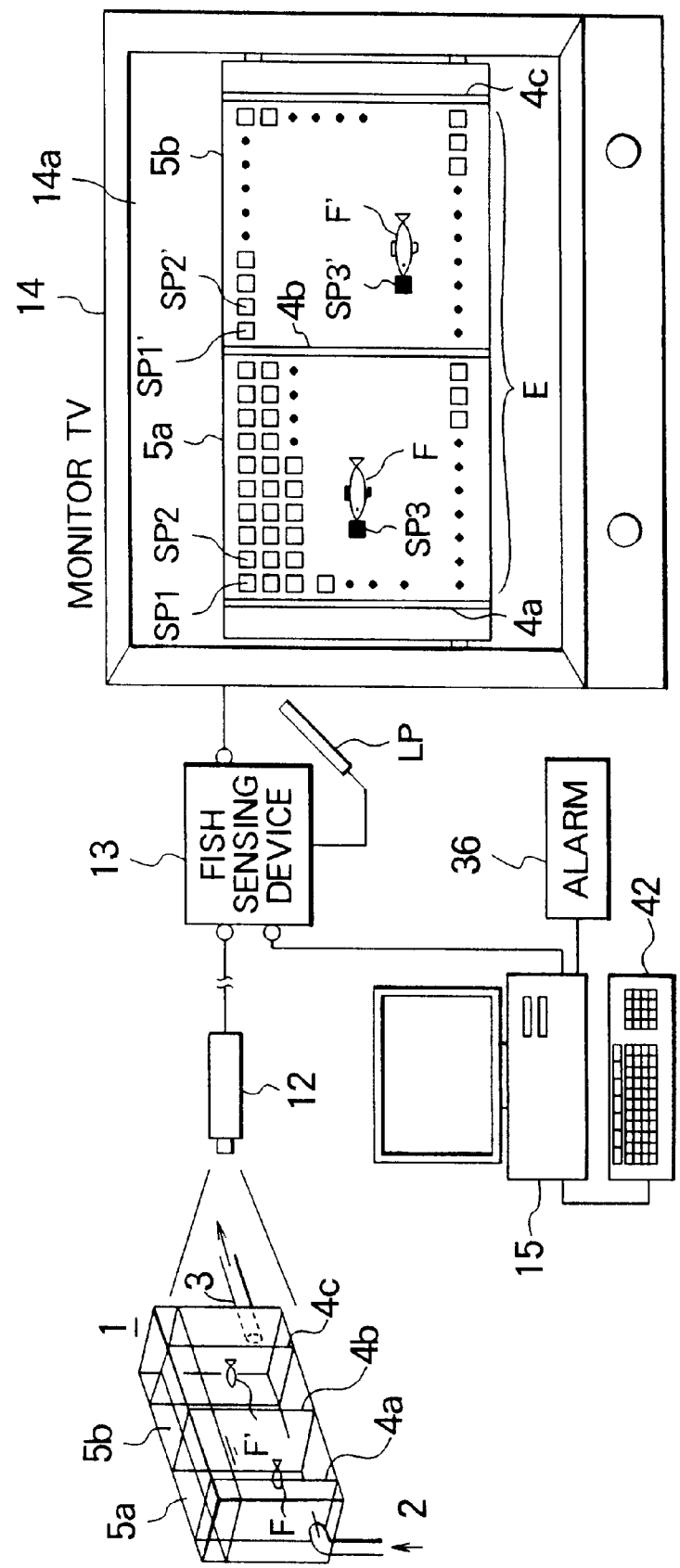
FIG. 1 is a block diagram showing the entire construction of a water quality monitoring apparatus using aquatic living things according to an embodiment of the present invention.
Figure 2A:
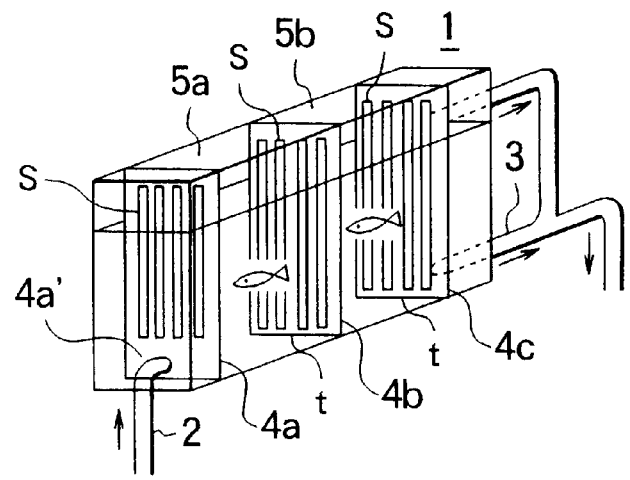
FIG. 2A is a perspective view showing a monitoring water tank of a water quality monitoring apparatus.
Figure 2B:
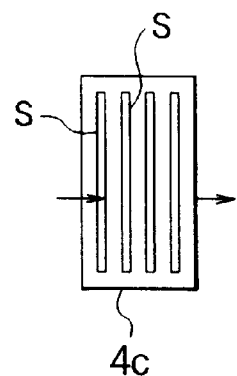
FIGS. 2B and 2C are front elevational views showing current or straightening plates within a monitoring water tank.
Figure 2C:
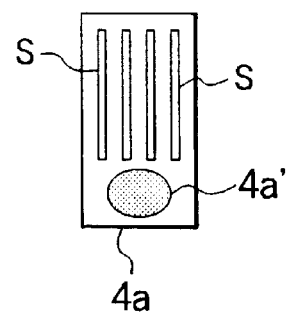
Figure 3:
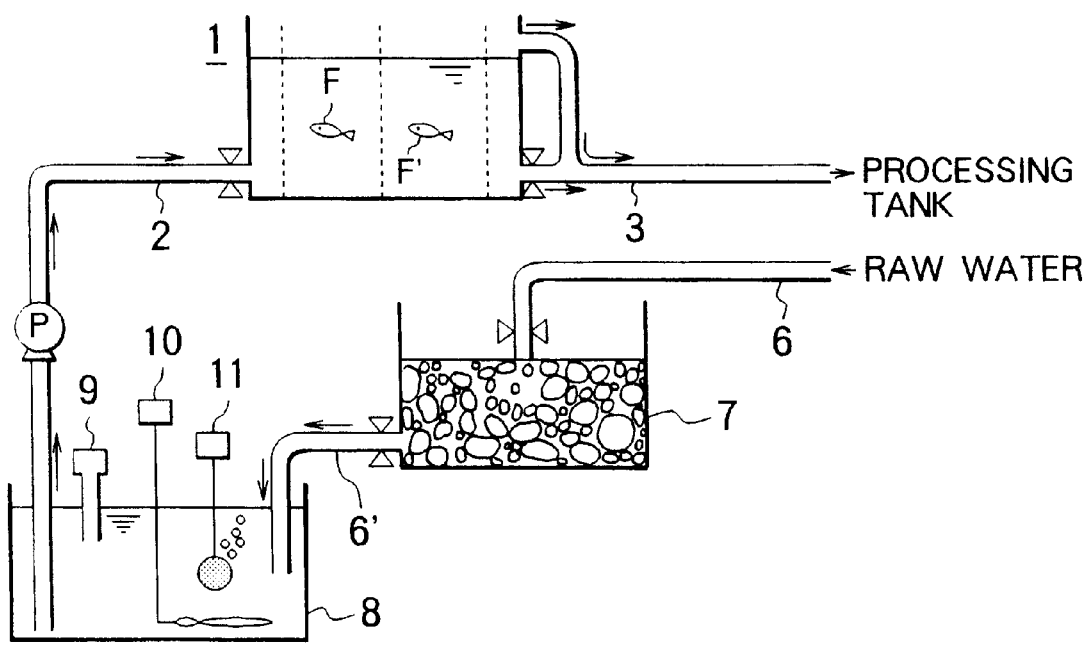
FIG. 3 is an illustration of a water flowing passage for raw water, leading to a monitoring water tank.

Referring now to the drawings, a description will be made hereinbelow of an embodiment of the present invention. In FIG. 1, numeral 1 represents a monitoring water tank having a transparent plate in at least its front surface side and made to receive, through a water supply pipe 2, raw water taken from a river, pond or the like and to continuously discharge the raw water from a water discharge pipe 3 to maintain a constant water level. The interior of the water tank 1 is partitioned into four sections by means of three perforated current or straightening plates 4a to 4c each having slits (through holes) S (see FIGS. 2A to 2C) which do not allow fish under observation to be transmittable. The raw water produces a water flow passing from the water supply pipe 2 through the slits S of the perforated current plates 4a to 4c each having a width of approximately 1 mm toward the water discharge pipe 3. Of the tank sections partitioned by the current plates 4a to 4c, the two central tank sections are used as first and second monitoring sections 5a, 5b and one fish F or F' (for example, killifish, carp, crucian carp) under observation being an aquatic living thing is raised within each of the first and second monitoring sections 5a, 5b. In addition, between the lower end portions of the current plates 4b, 4c and the lower surface of the water tank 1 there is defined a gap with a dimension of approximately 1 mm which is for the purpose of sending dust or the like contained in the raw water toward the water discharge pipe 3 side. Further, at a portion of the current plate 4a facing a water supply opening of the water supply pipe 2, a raw water receiving section 4a' having no slit is provided in order to block water bubbles, dust and others coming from the water supply pipe 2, thus preventing them from being introduced into the monitoring sections 5a, 5b. As shown in FIG. 3 the aforesaid raw water first passes through a water supply pipe 6 and, after dust or the like are removed through a filtration layer 7, flows through a connection pipe 6' and water reception tank 8 to be introduced by a pump P or the like through the aforesaid water supply pipe 2 into the monitoring tank 1. Still further, within the water reception tank 8 there are installed a bait supply device 9 for feeding bait, a heater 10 with a temperature adjusting device which keeps the water temperature of the raw water constant, and an aeration pump 11.

Furthermore, in FIG. 1, numeral 12 designates an industrial monitoring television camera (monitor camera) such as an ITV which is located on the front surface side of the monitoring water tank 1 to photograph the monitoring sections 5a, 5b. Further, numeral 13 depicts a fish sensing device (sensing means) which, for example, displays the images of the monitoring sections 5a, 5b on a television screen 14a of a monitor television 14 as shown in FIG. 1 and which successively outputs the position data on the observation fish F, F' in the respective monitoring sections 5a, 5b within the range of a monitoring area E set through a light pen (point setting means) LP. The aforesaid monitoring area E is formed in a manner that the light pen LP sets a plurality of sensor points SP1, SP2, SP1', SP2' within the range of the images of the monitoring sections 5a, 5b displayed on the monitor screen 14a, and the fish sensing device 13 detects the moving positions of the fish F, F' under observation on the basis of the luminance level variation of the sensor points within the monitoring area E.

Figure 11:
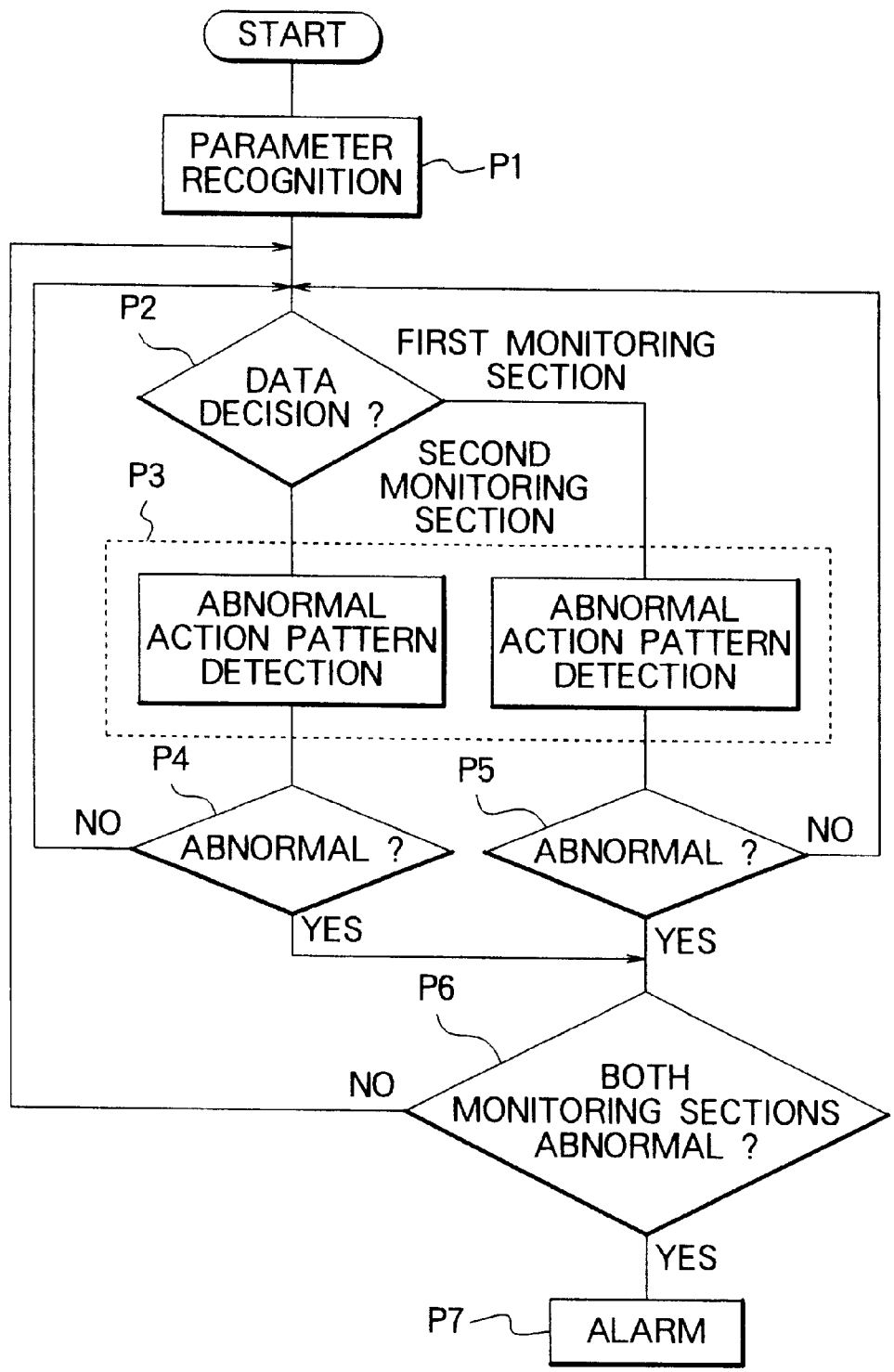
FIG. 11 is a flow chart showing a water quality monitoring operation of a microcomputer.

Furthermore, numeral 15 depicts a personal computer which receives the position data from the fish sensing device 13 to detect the action patterns of the fish F, F' under observation on the basis of the same position data in accordance with a processing procedure as shown in FIG. 11 and, when detecting the abnormality of the action pattern, operates an alarm 36 to issue an alarm indicative of the occurrence of the abnormality of water quality.

When the abnormality of water quality occurs, the observation fish F or F' in the monitoring section 5a or 5b takes three abnormal action patterns: a madly running action (a first abnormal action pattern shown in FIG. 4A) that the fish abnormally swims up and down and right and left directions at a high speed within the water tank 5a or 5b, an upward putting-out action (a second abnormal action pattern shown in FIG. 4B) that its swims in the vicinity of the water surface in a state where its mouth puts out above the water or goes in and out of the water surface, and an evasion action (a third abnormal action pattern shown in FIG. 4C) that it swims up and down in a place close to a drainage outlet in the water discharge pipe 3 side for a refuge from danger, i.e., in the vicinity of the current plate 4b in the case of the first monitoring section 5a or in the vicinity of the current plate 4c in the case of the second monitoring section 5b. In addition, the fish assumes a further abnormal action pattern; four abnormal patterns in total, that is, in the case of death, the fish takes an active state abnormality (a fourth abnormal action pattern shown in FIG. 4D) that it floats on the water surface in a state with turning up its belly. Incidentally, in the normal condition the fish assumes an action pattern (see FIG. 4E) that it swims at a constant relatively low speed within a range from the central portion of the water tank 5a or 5b toward the lower portion thereof.

Figure 5:
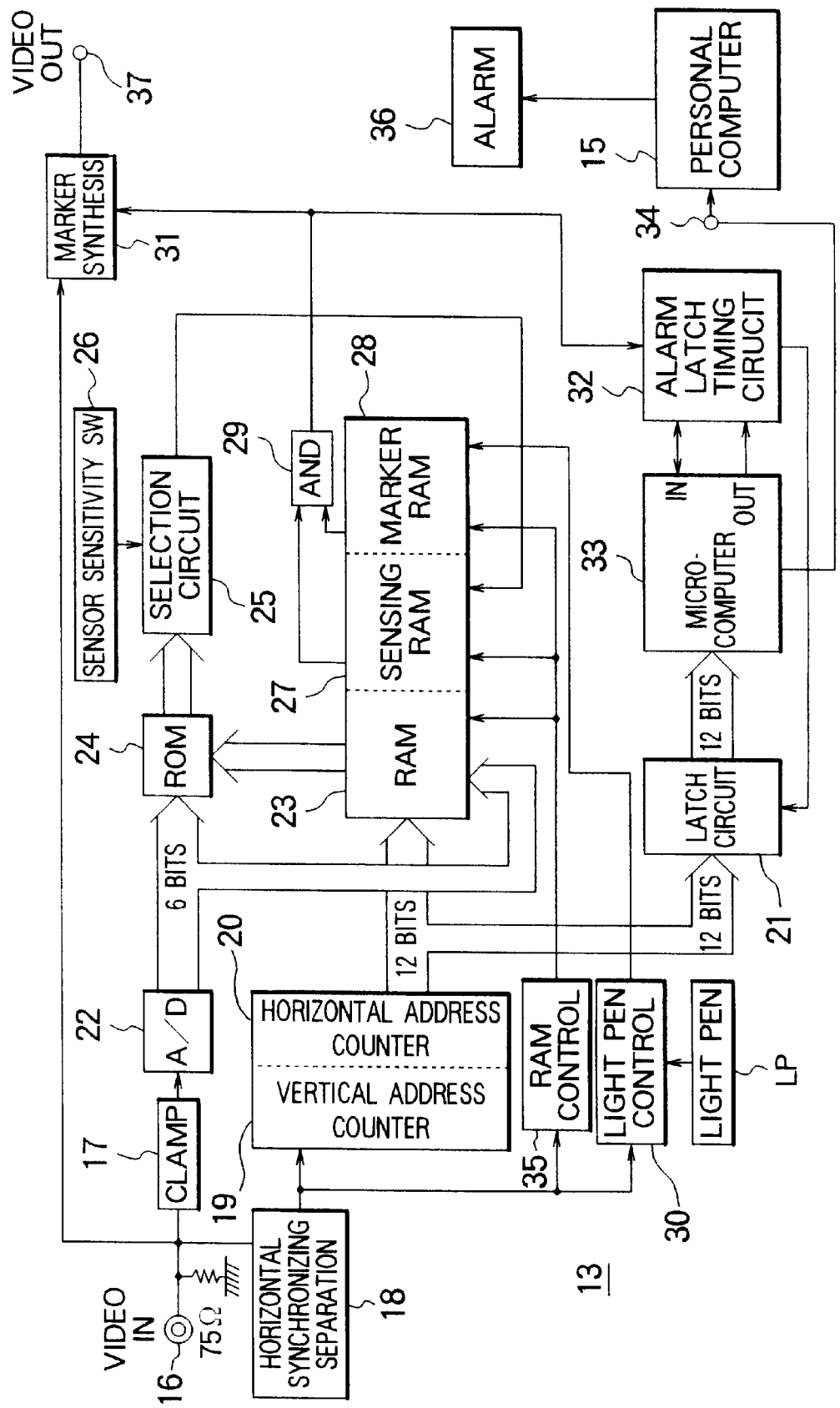
FIG. 5 is a block diagram showing a fish sensing device used for a water quality monitoring apparatus.
Figure 6:
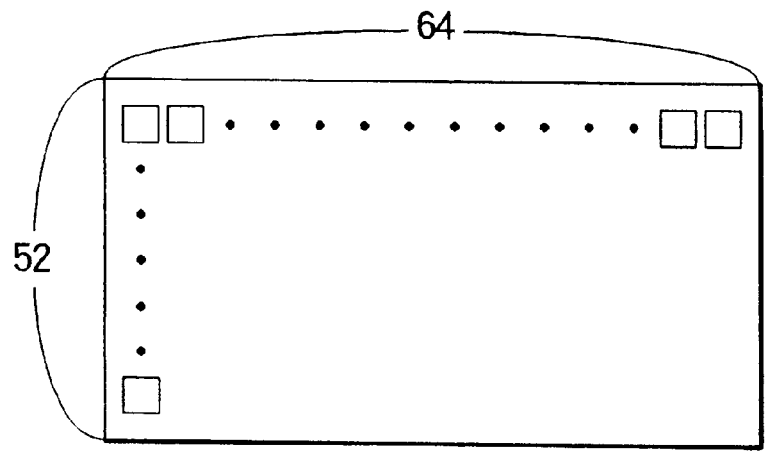
FIG. 6 is an schematic illustration of sensor points to be set on a monitor television of a water quality monitoring apparatus.

Secondly, referring to FIG. 5, a description will be taken hereinbelow of a detailed arrangement of the fish sensing device 13. Numeral 16 represents a video input terminal which receives a video signal from the aforesaid camera 12, and numeral 17 designates a clamp circuit which is for the purpose of pedestal-clamping the video signal to keep the voltage constant so that its sink level does not vary in response to the variation of an image and is for outputting a luminance signal. Further, numeral 18 depicts a horizontal synchronizing separation circuit for separating a horizontal synchronizing signal from the video signal, numeral 19 denotes a vertical address counter for vertically dividing one scene (field) into 52 lines on the basis of the horizontal synchronizing signal, and numeral 20 indicates a horizontal address oscillator for dividing a horizontal line of the one scene into 64 dots. These devices set sensor points (3328 points in total): 64 points in the horizontal directions and 52 points in the vertical directions in one scene (see FIG. 6), with they being assigned as addresses of a RAM 23 and all the sensor point positions being stored in the same RAM 23. The number of sensor points are not limited to this value, but it is also appropriate to use a different number of sensor points, for example, using more sensor points is acceptable.

In addition, numeral 21 stands for a latch circuit which receives, at every field, position data (address data) on each of the sensor points produced in the vertical address counter 19 and the horizontal address oscillator 20. The latch circuit 21 retains the position data on the sensor point (the position data on the sensor point producing luminance level variation), taken at the moment when an alarm signal which will be described later occurs, on the basis of the input of a latch signal (latch pulse) from an alarm latch timing circuit 32 caused by the alarm signal and further delivers the retained position data to a microcomputer 33. Further, numeral 22 represents a 60-bit A/D converter which converts the luminance signal into a digital signal to divide it into 64 steps or stages in concentration variation, with the digital signal produced by the A/D conversion being sent to a ROM 24 and the RAM 23 at every point.

Figure 7:
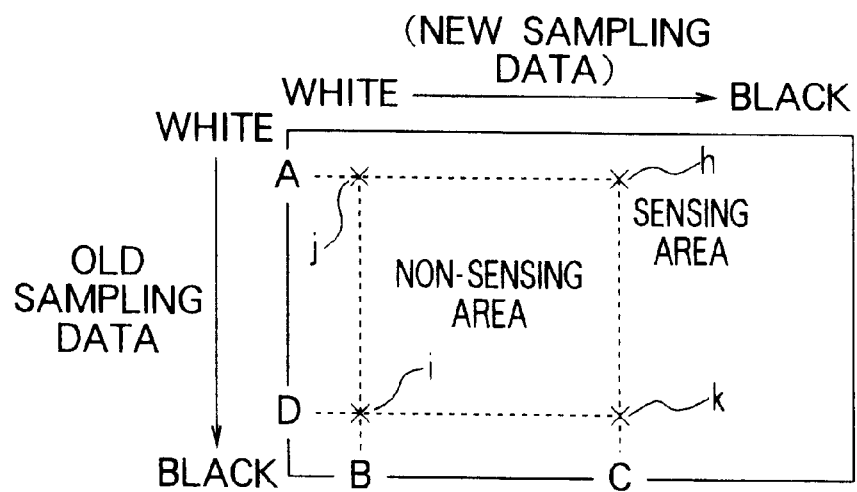
FIG. 7 is a conceptual illustration of the contents of reference codes in a ROM of a water quality monitoring apparatus.

Furthermore, numeral 23 designates the aforesaid RAM for storing the above-mentioned digital signal. The RAM 23 stores as sampling data the digital data corresponding to one field successively inputted and further updates the old sampling data once per three fields and delivers it to the aforesaid ROM 24. This comparison operation can also be conducted at a different field interval. Further, numeral 24 depicts the ROM in which a luminance level reference code shown in FIG. 7 is set in advance. The ROM 24 receives new sampling data from the A/D converter 22 and the old sampling data from the RAM 23. The ROM 24 compares the new sampling data with the old sampling data to check, on the basis of the reference code, whether or not the concentration variation (variation in luminance level) occurs on one sensor point. Concretely, when the fish F or F' under observation does not exist, the old sampling data at that sensor point comes to the vicinity (A) of the white level, and when the fish under observation moves so that the new sampling data at the corresponding sensor point becomes in the vicinity (C) of the black level, a decision to the concentration variation is made referring to a point h standing within the sensing range to output an alarm signal (8-bit output data) including a position signal on the sensor point. On the other hand, if the fish F or F' under observation is present, in that sensor point the old sampling data comes to the vicinity (D) of the black level, and after the same fish moves, the new sampling data at the same point shifts to the vicinity (B) of the white level, and hence a point i existing in the non-sensing range is used as the reference. In this case, the output of the alarm signal does not take place. Accordingly, the alarm signal arises in the case that the concentration variation occurs at the sensor point in the direction that the fish F or F' advances, whereupon the moving positions of the fish F, F' under observation are continuously detectable at the substantial real time. Needless to say, in the area where the fish F or F' does not exist, both the old and new sampling data stand in the vicinity of the white level and a point j existing within the non-sensing range is used as the reference. Further, in the case that the fish F, F' under observation stops to move, both the old and new sampling data stand in the vicinity of the block level and a point k existing within the non-sensing range is referred to. Thus, in both the cases, a decision is made to no concentration variation, so that the output of the alarm signal does not take place.

Still further, numeral 25 denotes a multiplexer selection circuit which selects the alarm signal inputted from the ROM 24, on the basis of the sensitivity set in a sensor sensitivity switch 26 and outputs only the alarm signal based upon the set sensitivity. The sensor sensitivity switch 26 can be made to set the alarm signal sensitivity in 8 steps, whereupon unreliable concentration variation is ignorable while only the sure concentration variation is detectable. Numeral 27 indicates a sensing RAM which once stores the alarm signal coming from the selection circuit 25 and writes its address in a marker RAM 28 and further output it to an AND circuit 29.

Figure 10A:
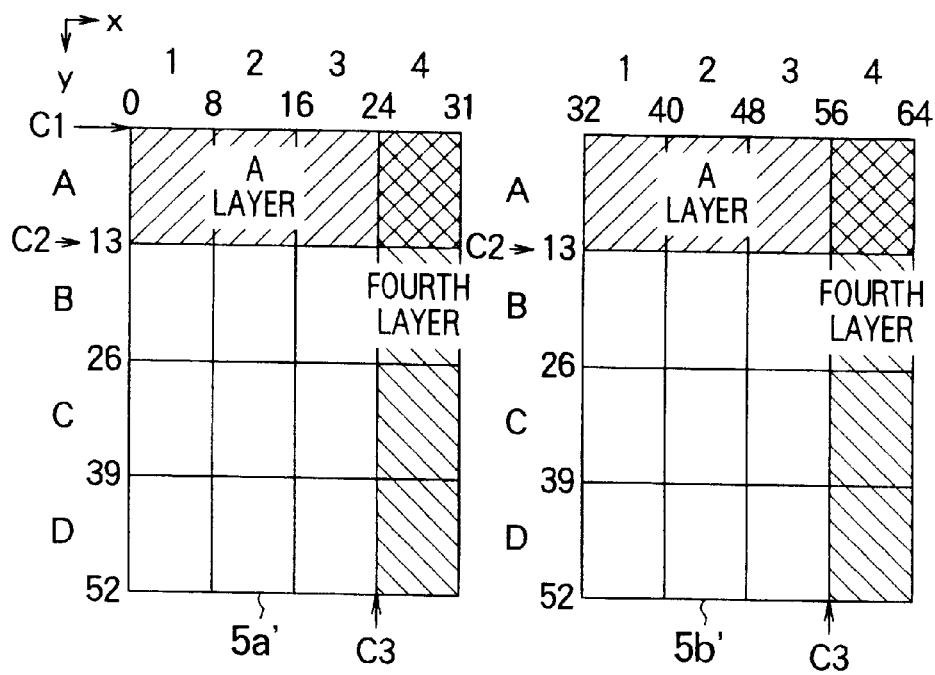
FIG. 10A is an conceptual illustration of a monitoring water tank recognized through a microcomputer.
Figure 10B:
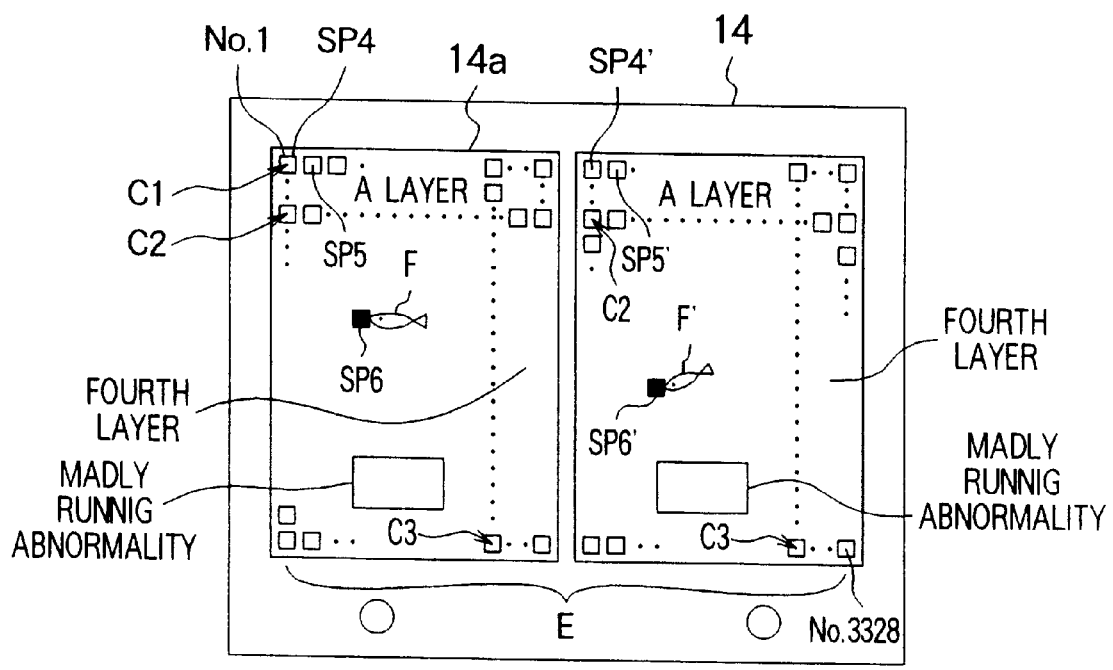
FIG. 10B is an illustration of a scene on a monitor television having set sensor points.

Moreover, numeral 30 denotes a light pen control circuit which is for sending, through said light pen LP, a marker position (the positions of the sensor points SP1, SP2, and others) set on a television scene to the marker RAM 28. The light pen LP detects electron light when being brought into contact with the monitor scene, and the detection signal is processed by an amplifier of the light pen LP up to the processing level and then taken in by the light pen control circuit 30. The marker RAM 28 stores the marker position set through the light pen LP and outputs it to the AND circuit 29. The light pen LP allows a monitoring area E to be set on the monitor television 14, for example, as shown in FIG. 1. Further, in cases where the monitoring water tank 1 is imaged on the entire television scene 14a as shown in FIG. 10B, it is also appropriate that all the 3,328 sensor points are set and the entire scene 14a is used as the monitoring area E.

Furthermore, numeral 29 stands for the aforesaid AND circuit for, in response to the reception of the alarm signal from the sensing RAM 27 due to a position coincident with the marker position stored in the marker RAM 28, sending the alarm signal to a marker synthesizing circuit 31 and an alarm latch timing circuit 32. That is, only when receiving the alarm signal due to a position coincident with the address position stored in the marker RAM 28, it is finally outputted as the alarm signal. The marker synthesizing circuit 31 adds the marker position indicated with the alarm signal to the video signal inputted from the video input terminal 16 in a state with being synchronized with the television scan and outputs the resultant to a video output terminal 37. Thus, as shown in FIG. 1 or FIG. 10B, the sensor point at which the concentration variation occurs inverts to block at display.

Still further, numeral 32 designates the aforesaid alarm latch timing circuit which issues a latch signal to the latch circuit 21 at the timing of the input of the alarm signal and retains the position data (the address data in the RAM 23) at the time of the input to the latch circuit 21. Numeral 33 depicts the aforesaid microcomputer which, when receiving the address data retained and sent in and from the latch circuit 21, converts the address data being the position data into parallel data and outputs the conversion result through a RS-232C output terminal 34 to the aforesaid personal computer 15. The parallel data indicates, of the sensor points, the point position where the luminance signal variation occurs as numeric data. For example, in the case of FIG. 1, in the first and second monitoring sections 5a, 5b, the sensor point positions on the scene where the concentration variation occurs are concretely shown with the X-Y coordinates such that SP3 point is taken as (X, Y)=(8, 20) and SP3' point is taken as (X, Y)=(30, 25). In the illustrations, numeral 35 represents a RAM control circuit for taking charge of the control of the RAMs 23, 27, 28, and numeral 36 depicts an alarm composed of a buzzer, an alarm lamp and others.

Figure 8:
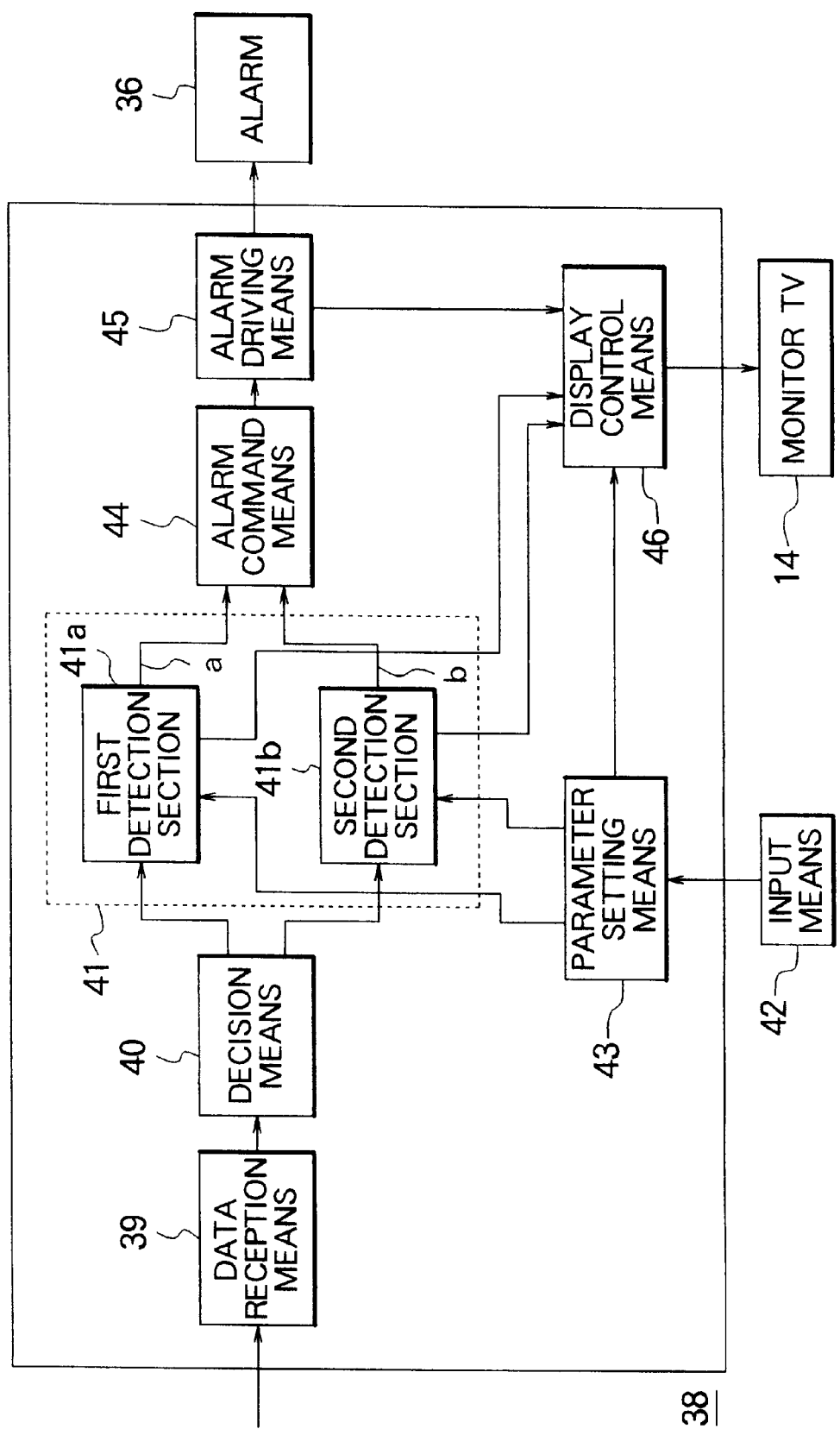
FIG. 8 is a block diagram showing a functional arrangement of a microcomputer of a water quality monitoring apparatus.

Furthermore, referring to FIGS. 8 and 9, a description will be made hereinbelow of a functional arrangement of a central control section 38 of the personal computer 15. FIG. 8 is a block diagram expressing the aforesaid control section 38 with function realizing means. In the same illustration, numeral 39 represents data reception means for receiving position data successively inputted from the aforesaid output terminal 34, and numeral 40 designates decision means which receives the same position data from the reception means 39 to decide, on the basis of a parameter (which will be mentioned later) about the monitoring area E, whether the same data is the position data of the first monitoring section 5a or the position data of the second monitoring section 5b. When the received data is the data on the first monitoring section 5a, the decision means 40 sends the position data to a first detection section 41a, and if the received data is the data on the second monitoring section 5b, it delivers the position data to a second detection section 41b.

Furthermore, numeral 41 denotes abnormal action pattern detecting means which analyzes the action pattern of the fish F or F' under observation in the first monitoring section 5a or the second monitoring section 5b on the basis of the decision result to check whether the action pattern is abnormal or not. The abnormal action pattern detecting means 41 comprises the first detection section 41a for analyzing the action pattern of the fish F on the basis of the position data on the first monitoring section 5a and the second detection section 41b for detecting the action pattern of the fish F' on the basis of the position data on the second monitoring section 5b. The first and second detection sections 41a, 41b substantially have the same function and are constructed with the function realizing means as shown in FIG. 9. The respective detection sections 41a, 41b decide the abnormal action patterns on the basis of various parameters set in input means 42 of the computer 15 in accordance with the predetermined processing procedure (see FIGS. 12 to 15). When detecting the abnormal action pattern of the fish F under observation, the detection section 41a continuously sends a first detection signal a including a signal specifying the abnormal action pattern to the next alarm command means 44 during the detection of the abnormal action patterns. On the other hand, when detecting the abnormal action pattern of the fish F' under observation, the detection section 41b sends a second detection signal b including a signal specifying the abnormal action pattern to the same alarm command means 44 in the same way. In addition, the respective detection sections 41a, 41b send to display control means 46 a display command signal indicative of the present monitored condition and the kind of abnormal action pattern.

Still further, numeral 42 represents the aforesaid input means for accepting various parameters necessary for the analysis in the above-mentioned abnormal action pattern detecting means 41, and numeral 43 designates parameter setting means for storing various parameters inputted and further for delivering the parameter data to the abnormal action pattern detecting means 41 and the display control means 46. Further, numeral 44 represents alarm command means which receives the first or second detection signal from the action pattern detecting means 41 and issues an alarm command signal only when receiving the first and second detection signals indicative of the abnormal action patterns from both the first and second detection sections 41a, 41b, that is, only when both the fish F and F' under observation in the first monitoring section 5a and the second monitoring section 5b take the abnormal action patterns (P6, P7 in FIG. 11). Accordingly, even if, for example, the fish F under observation in the one monitoring section 5a shows the normal state while only the second detection signal is inputted thereto, the output of the alarm command signal does not take place.

Moreover, numeral 45 depicts alarm driving means which sends a red lamp output signal and a buzzer output signal to the display control means 46 in response to the alarm command signal from the alarm command means 44 and further delivers an alarm driving signal to the alarm 36. Further, numeral 46 stands for the display control means receives various display command signals from the respective detection sections 41a, 41b and the aforesaid lamp output signals and others from the alarm driving means 45 to display various pictures on the monitor television 14 in accordance with these display commands.

Moreover, a description will be taken hereinbelow of an operation for setting various parameters necessary for the abnormal action pattern detection operation in the personal computer 15. Let it be assumed that the monitoring water tank 1 is photographed by the television camera 12 as shown in FIG. 1 and the monitoring water tank 1 is imaged on the television scene 14a as shown in FIG. 10B. In this state, the monitoring area R is set through the light pen LP on the television scene 14a. In this embodiment, for simplification of the description, the monitoring water tank 1 is imaged on the entire television scene 14a as shown in FIG. 10B and all the sensor points (1 to 3328 points) are set as the monitoring area E. In this case, it is also possible that as described before the monitoring water tank 1 is image on a portion of the monitor scene 14a (see FIG. 1) and the sensor points are set corresponding to the image of the monitoring water tank 1.

First, the "parameters about monitoring area E" are inputted through the input means 42 so that the personal computer 15 can recognize the monitoring area E set through the light pen LP. As shown in FIG. 10A the personal computer 15 sets a first monitoring section 5a' and a second monitoring section 5b' corresponding to the two monitoring sections 5a, 5b and is made to recognize both the monitoring sections on the X, Y coordinate in a state where a left and upper portion of the first monitoring section 5a' is set as the origin (0, 0). More specifically, the recognition can be made in a manner that the first monitoring section 5a' covers points 0 to 31 in the X-axial direction and points 0 to 52 in the Y-axial direction, and that the second monitoring section 5b' covers points 32 to 64 in the X-axial direction and points 0 to 52 in the Y-axial direction.

Moreover, the recognition can be made in a way that each of the monitoring sections 5a', 5b' is divided into four areas, i.e., first to fourth layers, along the X-axial direction and further divided into four areas, i.e., A to D layers, in the Y-axial direction. In this instance, as the parameters there are inputted the positions (X, Y) corresponding to the coordinate C1 indicative of the height of the water surfaces in the monitoring sections 5a', 5b', the coordinate C2 representative of the lower limit position of the region of the A layer (first layer) in the horizontal direction in the vicinity of the water surface and the coordinate C3 setting the width of the fourth layer (second layer) in the vertical direction in the vicinity of the current plates 4b, 4c on the water discharge outlet sides of the respective monitoring sections 5a, 5b. In this embodiment, the coordinate C1 is set to (0, 0) acting as the origin, the coordinate C2 is set to (0, 13) in the case of the first monitoring section 5a' and to (32, 13) in terms of the second monitoring section 5b', and the coordinate C3 is set to (24, 52) for the first monitoring section 5a' and to (56, 52) for the second monitoring section 5b'. Thus, the abnormal action pattern detecting means 41 can recognize the positions of the A layer and the fourth layer in terms of each water tank. The positions of the A layer and the fourth layer serve as the reference positions in recognizing the position of the fish F or F' under observation in the case of the detection of the upward putting-out action and the evasion action. Naturally, the respective parameters can arbitrarily be set corresponding to the dimension of the monitoring water tank 1 imaged on the monitor scene 14a.

Secondly, the input of "parameters for detection of abnormal actions" for the abnormal action patterns of the fish under observation, i.e., the madly running action, the upward putting-out action, evasion action and the active state abnormality, is made through the input means 42. First, for the madly running action, as the parameters there are set a madly running start speed, a monitoring period of time and the number of passing points (moving distance) (see FIGS. 9 and 12). Of these parameters, the madly running start speed signifies the swimming speed of the fish F or F' under observation, and when exceeding this speed, a decision is made to that the madly running action starts, whereupon a command for the display of "confirmation of the madly running action" (P11, P12 in FIG. 12) is generated so that the operation gets into a monitoring condition (P13). The speed of the fish under observation is calculated by the first detection means 41a or the second detection means 41b in accordance with the equation (speed)=(the number of passing points in the X-axial direction+the number of passing points in the Y-axial direction) / time taken for movement (seconds) as a function of the input interval of the position data and the number of points by which the fish under observation passes in terms of the same monitoring tank. The monitoring period of time is the time period taken for continuous monitoring after the confirmation of the start of a madly running action, while the number of passing points corresponds to the moving distance of the fish under observation. When the moving distance of the fish under observation comes to above this number of points for the monitoring time period, a decision is made to the madly running action (P14 to P16), and if the moving distance of the fish under observation is below this number of points for the monitoring time period, a decision is made to no occurrence of the madly running action (P14, P20). In this embodiment, as one example, the madly running start speed is set to be 100 points (P)/sec, the monitoring time period is set to 10 sec, and the number of passing points (moving distance) is set to 200 points.

Figure 9:
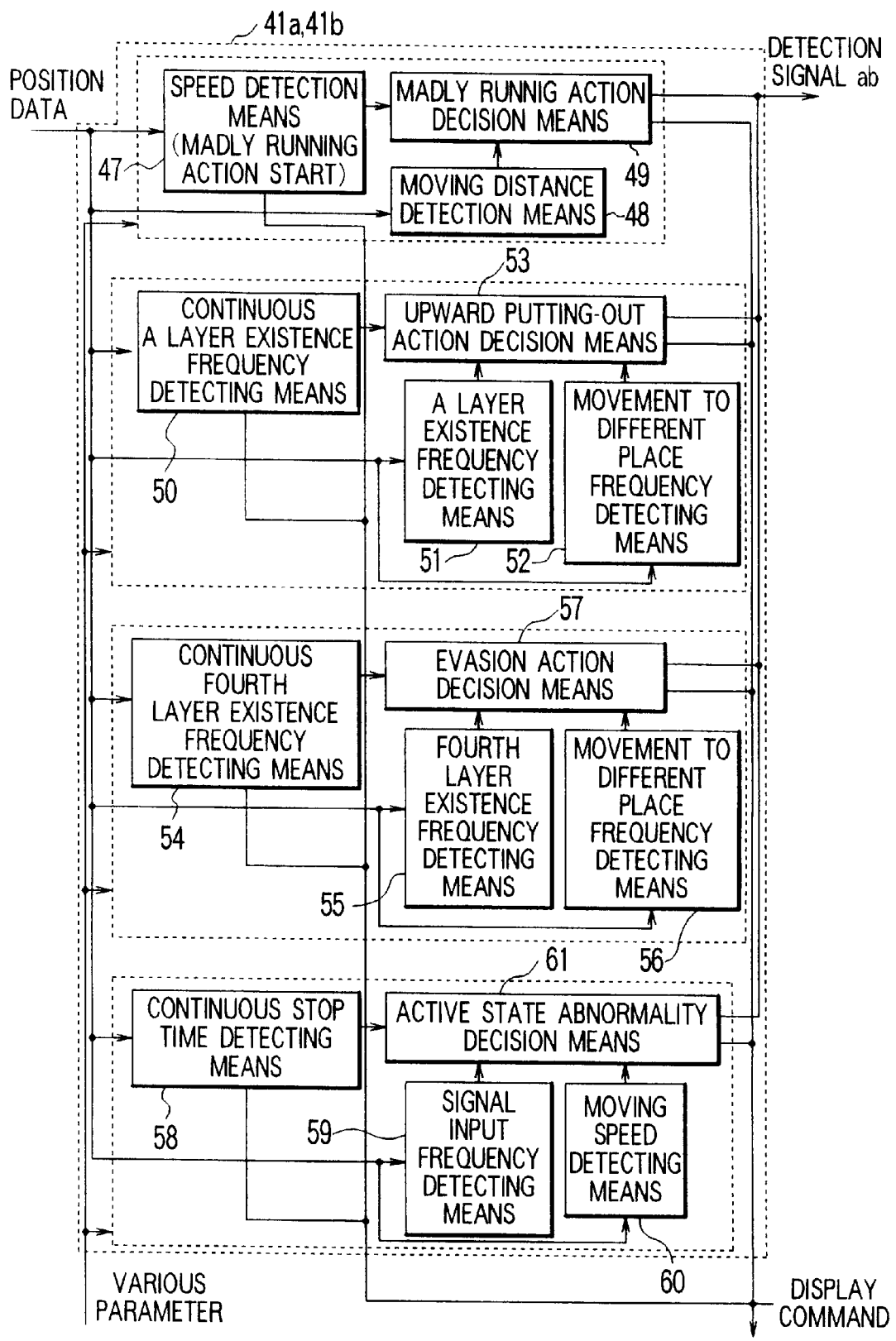
FIG. 9 is a block diagram showing a detection section of a microcomputer.
Figure 13:
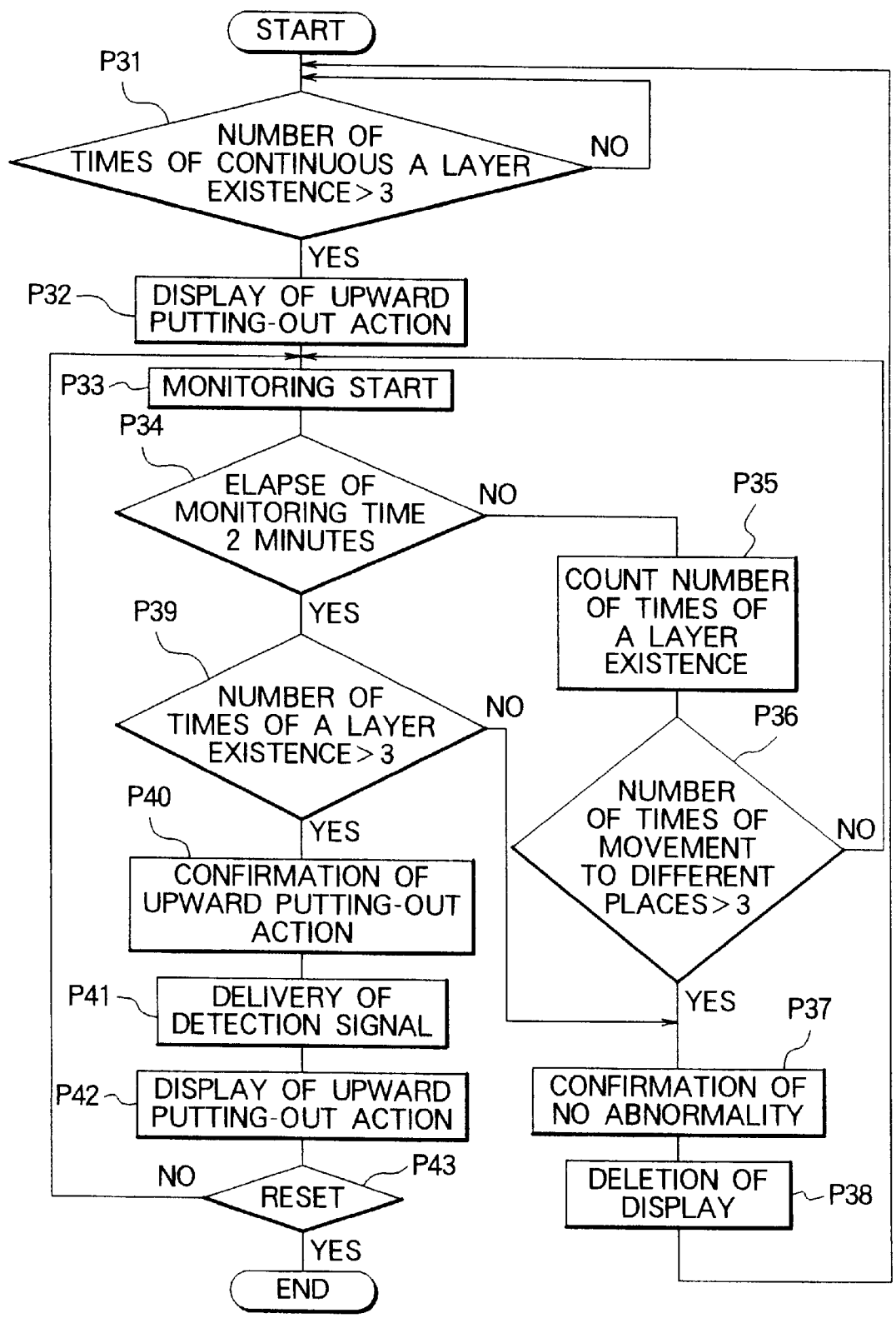
FIG. 13 is a flow chart showing an operation for detecting an upward putting-out action.

In the case of the upward putting-out action, as parameters there are set the number of times (frequency) of continuous A layer existence, the number of times of existence, the monitoring time period and the number of times of movement to different places (see FIGS. 9 and 13). Of these parameters, the number of times of continuous existence in the A layer signifies the number of times of the fact that the fish under observation continuously stands within the range of the above-mentioned A layer. If exceeding this value, the start of the upward putting-out action is judged so that a command for the display of "confirmation of the upward putting-out action" is issued (P31, P32 in FIG. 13), with the result that the operation comes into the monitoring state (P33). The monitoring time period is the time period taken for the continuous monitoring after the confirmation of the start of the upward putting-out action. Further, the number of times of existence is the number of times of the fact that the fish under observation stands in the A layer for the monitoring time period. After the elapse of the monitoring time period a judgment is made whether or not the number of times exceeds this value. If exceeding this value, a decision is made to the upward putting-out action and the "upward putting-out action" is displayed (P34, P39 to P42). The number of times of continuous existence signifies the number of times of the fact that the position data within the A layer is continuously inputted to the first or second detection means 41a or 41b, and for example if the fish F, F' under observation stand within the A layer for a given period of time, the position data on the same fish results in being inputted thereto. The number of times of movement to different places is the number of times of the fact that the fish moves to portions other than the A layer. When exceeding a set value for the monitoring time period, a decision is made to no occurrence of the upward putting-out action (P36, P37, P38). The number of times of stop is also detectable by counting the position data other than the position data in the A layer. If the fish under observation stays at an arbitrary position other than the A layer for a given period of time, that position data is continuously inputted thereto. In this embodiment, as one example, the number of times of continuous existence in the A layer is set to 3, the monitoring time period is taken to be 2 minutes, and the number of times of movement to different places is taken to be 3.

Figure 14:
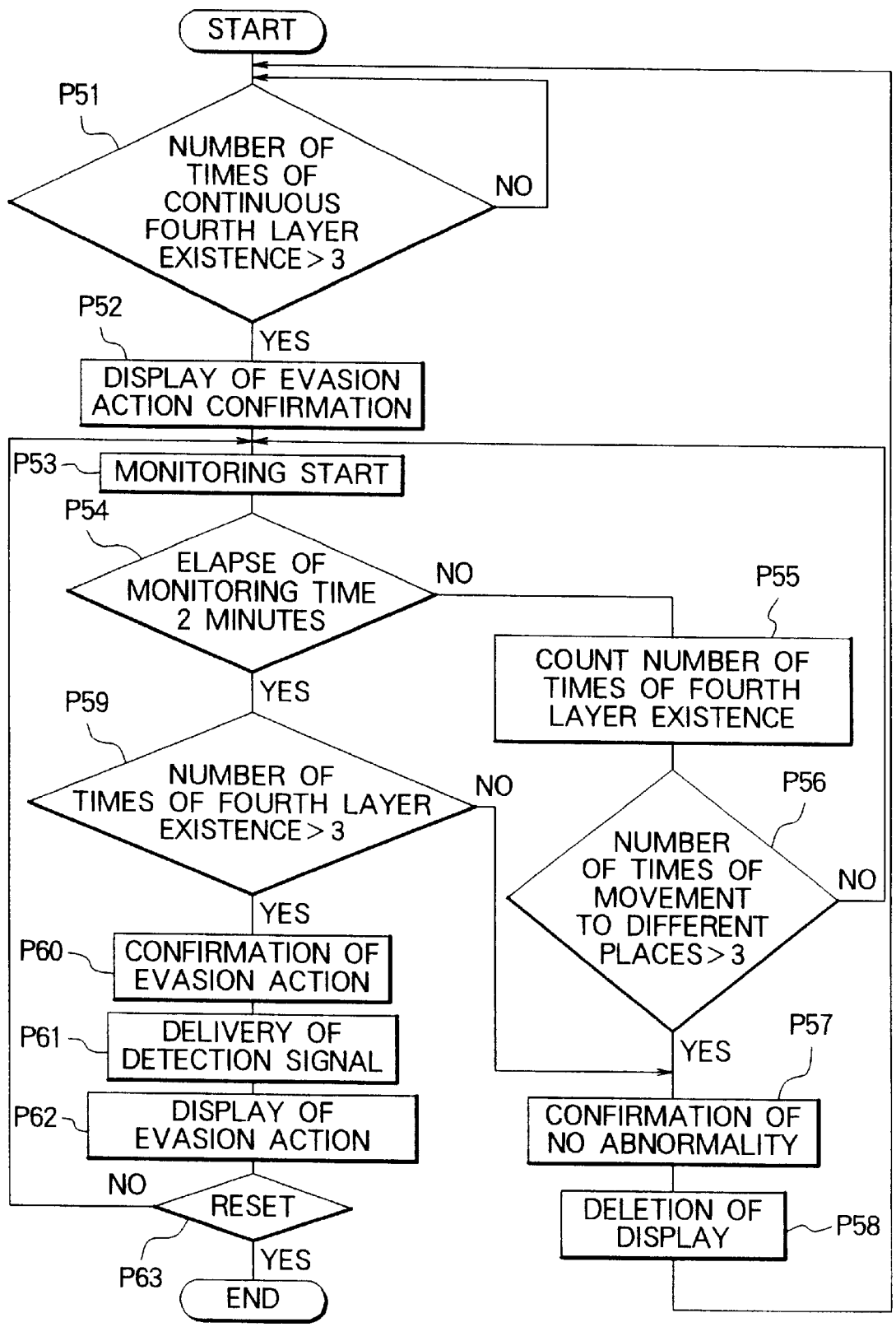
FIG. 14 is a flow chart showing an operation for detecting an evasion action.

In the case of the evasion action, as parameters there are set the number of times of continuous existence in the fourth layer, the number of times of existence, a monitoring time period and the number of times of movement to different places (See FIGS. 9 and 14). Of these parameters, the number of times of continuous existence in the fourth layer signifies the number of times of the fact that the fish under observation stands within the range of the fourth layer, and if exceeding this value, a decision is made to the start of the evasion action, so that "confirmation of evasion action" is displayed and the fish under observation gets into the monitored state (P51, P52, P53 in FIG. 14). The monitoring time period is the time taken for the monitoring after the confirmation of the start of the evasion action and the number of times of existence is the number of times of the fact that the fish under observation exists for the monitoring time period. After the elapse of the monitoring time period, a judgment is made on whether or not this value exceeds a set value. If exceeding the set value, a decision is made to the occurrence of the evasion action, with the result that "evasion abnormality" is displayed (P 54, P59 to P 62). As well as the case of the upward putting-out action, the number of times of continuous existence signifies the number of times of the fact that the position data within the fourth layer is continuously inputted to the first or second detection means 41a or 41b, and the number of times of existence is counted on the basis of that position data. The number of times of movement to different places is the number of times of the fact that the fish under observation moves to or stands at different portions other than the fourth layer. When exceeding a set value for the monitoring time period, a decision is made to no evasion abnormality (P54, P55 to P57). In this embodiment, as one example, the number of times of continuous existence in the fourth layer is taken to be 3, the number of times of existence is taken to be 3, the monitoring time period is set to 2 minutes, and the number of times of movement to different places is set to 3.

Figure 15:
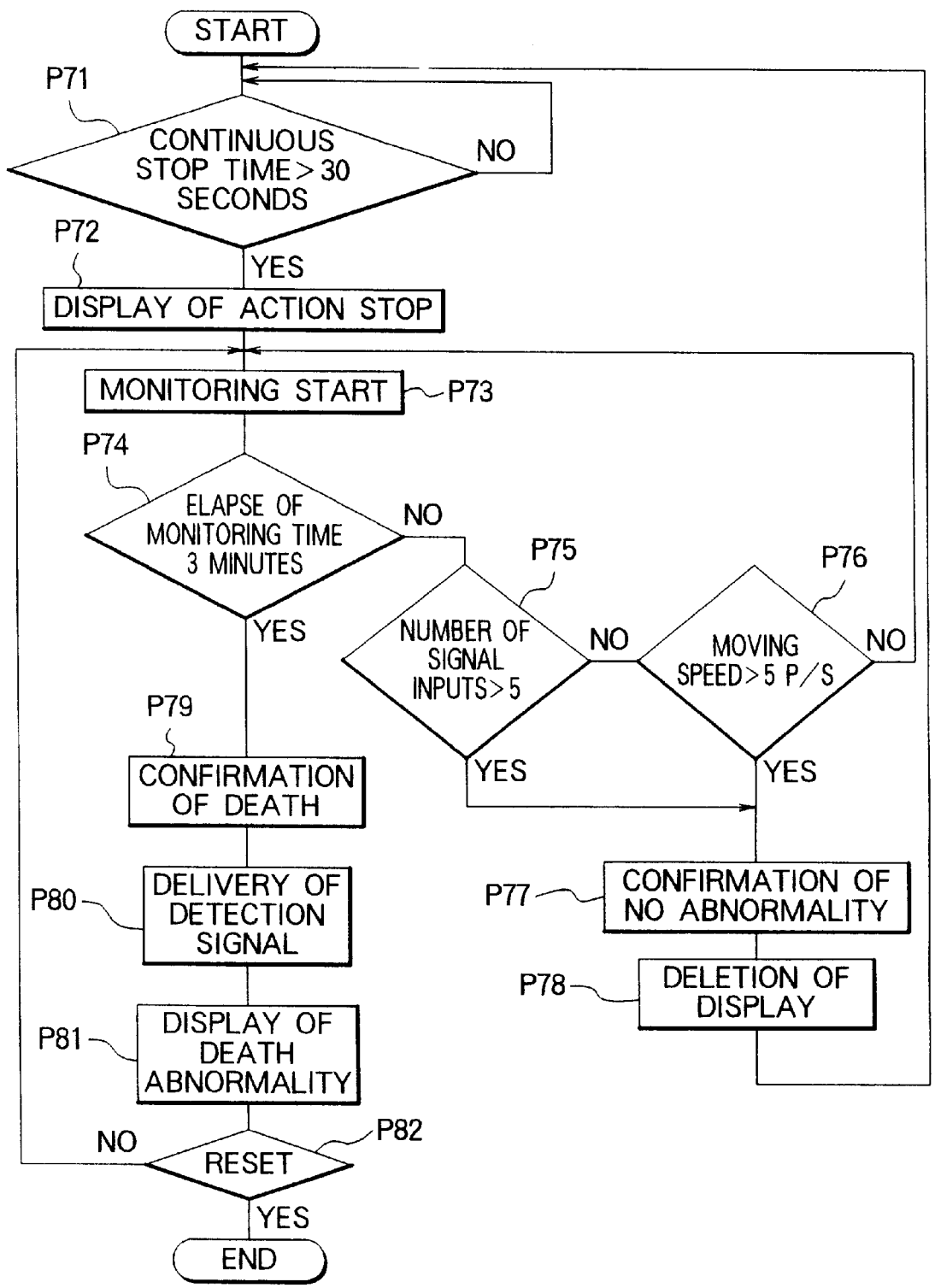
FIG. 15 is a flow chart showing an operation for detecting an abnormality of active state.

In the case of the active state abnormality, as parameters there are set a continuous stop time period, a monitoring time period, the number of signal inputs and a moving speed (see FIGS. 9 and 15). The continuous stop time period is the time that the fish under observation continuously stays at a given place, that is, the time that the variation of the luminance signal stops and the input signal from the fish sensing device 13 does not take place. If such a state exceeds a set value, a decision is made to that the action stops, so that "action stop" is displayed to cause the operation to get into the monitoring condition (P71 to P73 in FIG. 15). The monitoring time period is the time taken for monitoring after the confirmation of the action stop, while the number of signals inputs corresponds to the number of times of the fact that the generation of the input signal from the fish sensing device 13 takes place, and even the moving speed is the speed at which the fish under observation swims in the monitoring condition. In the case that the number of signal inputs exceeds a set value or the moving speed becomes higher than a set value for the monitoring time period, a decision is made to no abnormality, with the result that the display indicative of "action stop" disappears (P74 to P78). On the other hand, in cases where both the number of signal inputs and moving speed are below the set values, a decision is made to the active state abnormality (P79). In this embodiment, as one example, the continuous stop time is set to be 30 seconds, the monitoring time period is set to 3 minutes, the number of signal inputs is set to 5 and the moving speed is set to 5 points/sec. Incidentally, the set parameter values are not limited to the above description but can appropriately be set taking into consideration the natures of the fish under observation and others.

Thus, the respective parameters set through the input means 42 are delivered through the parameter setting means 43 to the first and second detection means 41a, 41b (P1 in FIG. 11), and when receiving a parameter display command from the input means 42, the parameter setting means 43 displays, through the display control means 46, the parameters on the monitor television 14.

Moreover, a description will be taken hereinbelow of an operation of this apparatus in which the parameters are set as described above. A video signal inputted through the video input terminal 16 after the photography of the monitoring water tank is pedestal-clamped by the clamp circuit 17, and the luminance signal is converted into a digital signal at every field in the A/D converter 22. In addition, the address counter 19 and the address oscillator 20 set the 3328 sensor points on one scene which are simultaneously assigned as the addresses of the RAM 23, with the addresses of the sensor points being always sent to the latch circuit 21 at every field.

The sampling data for one field sampled in the A/D converter 22 are successively sent to the ROM 24 and the RAM 23, and the ROM 24 compares the new sampling data inputted from the A/D converter 23 with the old sampling data inputted from the RAM 23 on the basis of the luminance level reference code (see FIG. 7). In this case, in the area where the fish F or F' under observation does not exist, the variation in luminance level does not occur between the new and old sampling data, and hence a decision is made to no concentration variation. Accordingly, in this instance, the output of the alarm signal does not take place. On the other hand, in the case that the fish F or F' under observation swims while crossing the sensor points in the monitoring section 5a or 5b, since the fish F or F' under observation crosses one sensor point, the luminance level variation of the same point is detectable, so that referring to the point h in the sensing range of the reference code the alarm signal is outputted to the multiplexer selection circuit 25. Thus, if both the two fish F, F' under observation do not move, the comparison operation for one field produces the alarm signal due to the movement of the fish F under observation in the first monitoring section 5a and the alarm signal due to the movement of the fish F' under observation in the second monitoring section 5b.

In the multiplexer selection circuit 25, a decision is made of whether or not the above-mentioned alarm signal coincides with the sensitivity set in the sensor sensitivity switch 26. If being coincident with that sensitivity, the aforesaid alarm signal is forwarded to the sensing RAM 27. The sensing RAM 27 stores the alarm signal at the corresponding address position and further outputs it to the AND circuit 29. On the other hand, the aforesaid marker RAM 28 stores the positions of the sensor points (in this embodiment, all the sensor points) written through the light pen LP, with that position signal being outputted to the AND circuit 29. When receiving the alarm signal from the sensing RAM 27, the AND circuit 29 detects the coincidence of the position of that sensor point with the position of the sensor point inputted from the marker RAM 28 and further forwards the alarm signal to the marker synthesizing circuit 31 and the alarm latch timing circuit 32. The marker synthesizing circuit 31 adds a marker signal synchronizing with the television scan to the video signal on the basis of the input of the aforesaid alarm signal. Accordingly, on the television scene 14a the positions of the sensor points (in this case, the sensor points SP6, SP6' at the positions where the fish F, F' under observation exist) at which the concentration variation occurs, as shown in FIG. 10B) are inverted, for example, to black and displayed. Accordingly, the positions of the fish F, F' under observation which are on the movement are always displayed through the inversion of the sensor points.

In addition, the alarm latch timing circuit 32 sends a latch signal to the latch circuit 21 on the basis of the input of the aforesaid alarm signal. In response to the input of this latch signal, the latch circuit 21 retains the address data corresponding to the concentration variation at the moment when the alarm signal occurs, i.e., the address data of SP6 and SP6' and further sends the same data to the microcomputer 33. In the microcomputer 33, the address data is converted into parallel data (the position data on the X, Y coordinate) and then outputted to the RS-232C output terminal 34.

Figure 4A:
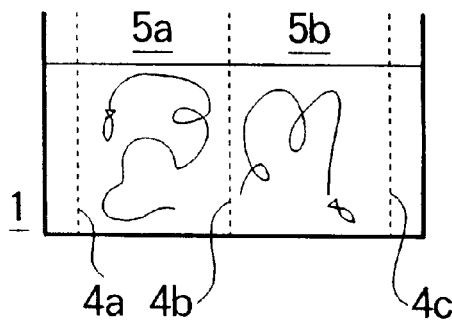
FIGS. 4A to 4F are illustrations of action patterns of fish under observation within a monitoring water tank.
Figure 12:
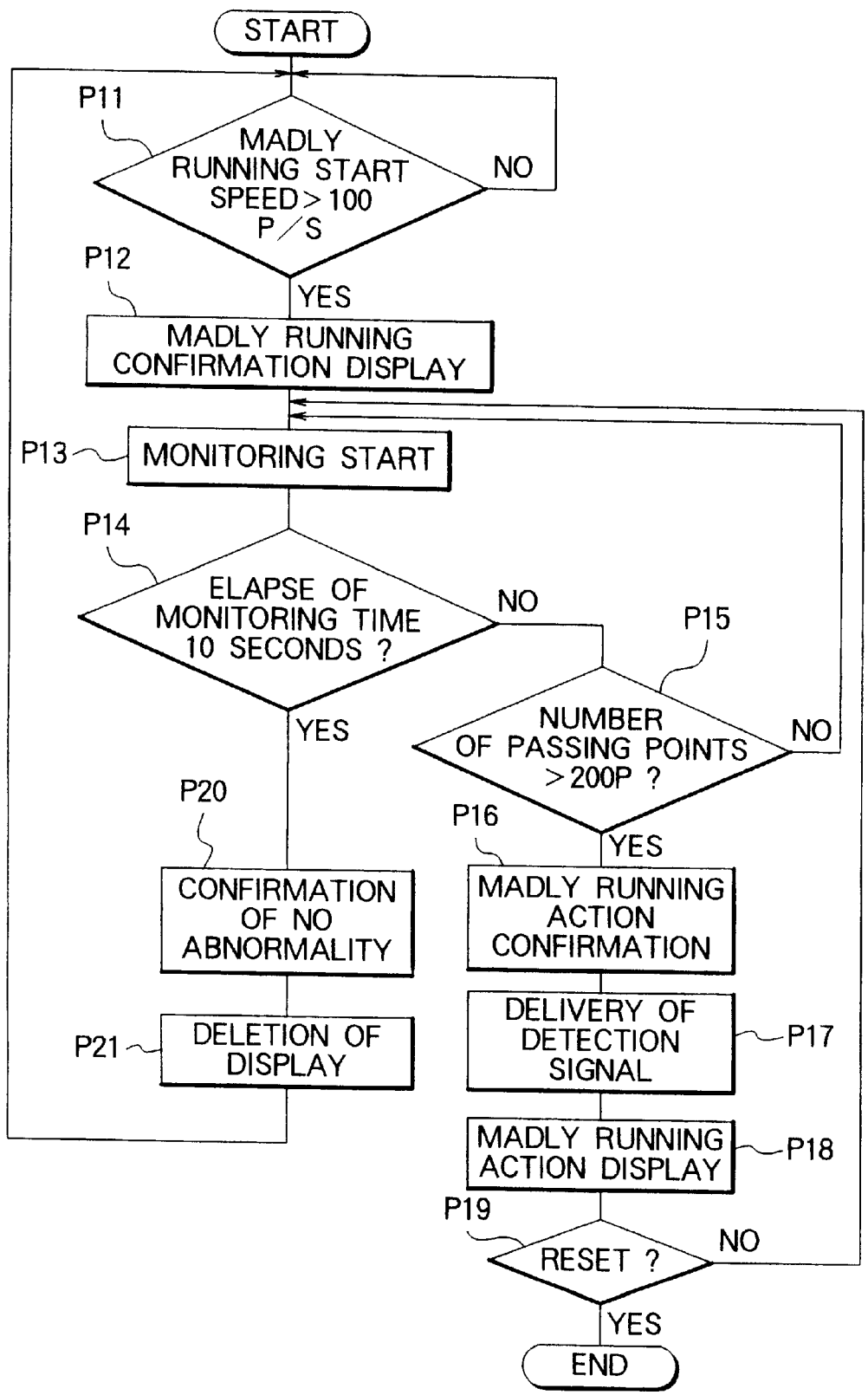
FIG. 12 is a flow chart showing an operation for detecting a madly running action.

In cases where the fish F, F' under observation swim and move in the monitoring water tanks 5a, 5b, the above-mentioned position data is continuously outputted from the output terminal 34 to the personal computer 15, and the position data are successively inputted to the data reception means 39 of the computer 15. The data reception means 39 sends the inputted position data to the decision means 40, whereas the decision means 40 checks, on the basis of the inputted position data, whether that position is in the first monitoring section 5a or in the second monitoring section 5b. In addition, on the basis of the decision result, it successively sends the position data to the first detection section 41a if being the position data on the first monitoring section 5a and successively sends the position data to the second detection section 41b if being the position data on the second monitoring section 5b (P1 to P3 in FIG. 11). Further, both the detection means 41a, 41b individually detect the occurrence or no occorrence of the abnormal action patterns: the madly running action, the upward putting-out action, the evasion action and the active state abnormality in the first and second monitoring sections 5a, 5b. The first and second detection sections 41a, 41b judge the abnormal action patterns of the fish F, F' under observation in accordance with the following procedure. Since the first and second detection sections 41a, 41b perform the same monitoring operation, for the convenience, in the description the monitoring operations of both the detection sections 41a, 41b are independently conducted on the basis of the position data inputted.

i) Detection of Madly Running Action (the first monitoring operation, see FIGS. 9, 12 and 4A)

Figure 4B:
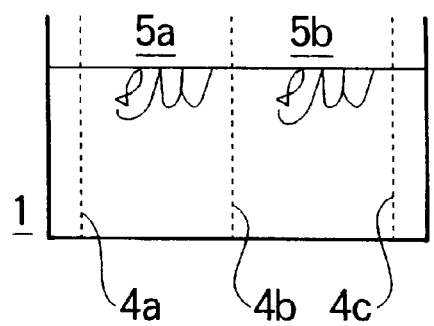

On the basis of the set parameters, a speed detection means 47 of the first or second detection means 41a or 41b checks whether or not the speed of the fish F or F' under observation exceeds the madly running start speed (100 P/S). If the speed of the observation fish exceeds 100 P/S (P11 in FIG. 12), on the basis of the decision to that the madly running action starts, the speed detection means 47 issues a command for the display of "confirmation of madly running action" toward the display control means 46, with the result that the system gets into the madly running action monitoring state (P12, P13). In accordance with the aforesaid display command, the display control means 46 displays the "the confirmation of the madly running action" on the television scene 14a. After the start of monitoring, a madly running action decision means 49 checks, on the basis of the detection by moving distance detection means 48, whether or not the number of passing points exceeds 200 P for a monitoring time period (10 seconds) (P14, P15). If the number of passing points exceeds 200 P for the monitoring time period, the occurrence of the madly running action is decided, so that the first detection section 41a sends a first detection signal indicative of the madly running action to the alarm command means 44 while the second detection means 41b sends a second detection signal representative of the madly running action thereto (P16, P17). Further, a display command for "madly running abnormality" is issued to the display control means 46 (P18), whereupon the "madly running abnormality" appears on the television scene 14a (see FIG. 10B). The detection signal sending operation and the display command operation continue during the detection of the abnormal action pattern due to the madly running action. In the case that the number of passing points does not exceed 200 P even after the monitoring time period, a decision is made to no abnormality (P20), with the result that a command for cancelling the display of the "confirmation of madly running action" is issued (P21) so that the display "confirmation of madly running action" disappears on the television scene 14a.

ii) Detection of Upward Putting-out action (a second monitoring operation, see FIGS. 9, 13 and 4B)

Figure 4C:
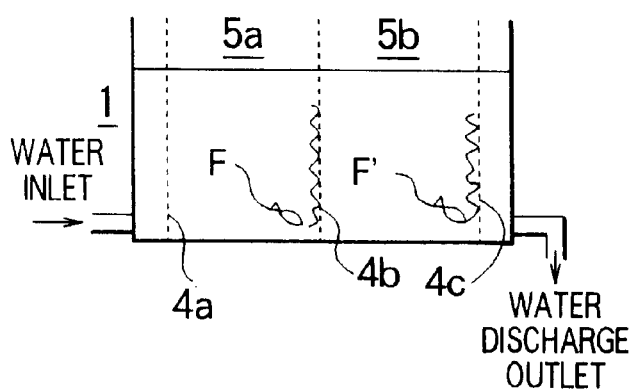

On the basis of the set parameters a continuous A layer existence frequency detecting means 50 detects or checks whether or not the number of times of the fact that the fish F or F' under observation continuously exists within the A layer exceeds 3 (P31 in FIG. 13). If the detection shows that the frequency exceeds 3, a decision is made to that the fish starts the upward putting-out action, so that it issues a command for the display of "confirmation of upward putting-out action" to the display control means 46, thus getting into the upward putting-out action monitoring condition (P32, P33). In accordance with the display command the display control means 46 displays "confirmation of upward putting-out action" on the television scene 14a. After the start of the monitoring operation, A layer existence frequency detecting means 51 counts the number of times of the fact that the fish exists within the A layer for the monitoring time period and movement-to-different-place frequency detecting means 52 counts the number of times of the fact that the fish exists in places other than the A layer (P34, P35, P36), and if the number of times of existence in places other than the A layer within 2 minutes exceeds a set value, an upward putting-out action decision means 53 makes a decision to no abnormality even if the number of times of existence in the A layer exceeds the set value (3), and further issues a command for the deletion of "confirmation of upward putting-out action" to the display control means 46 (P36 to P38), so that the display "confirmation of upward putting-out action" on the television scene 14a disappears. In the case that the number of times of movement to difference places is below the set value for the monitoring time period (2 minutes), after the elapse of the monitoring time period, it judges whether or not the number of times of existence in the A layer exceeds the set value (3) (P39), and if exceeding the set value, a decision is made to the occurrence of the upward putting-out abnormality (P40), and the first detection section 41a outputs the first detection signal indicative of the upward putting-out action to the alarm command means 44, while the second detection section 41b sends the second detection signal indicative of the upward putting-out action to the same alarm command means 44 (P41). In addition, the display command for the "upward putting-out abnormality" is sent to the display control means 46 (P42) so that the display "upward putting-out abnormality" appears on the television scene 14a. The delivery of the detection signals and the display command continue during the detection of the upward putting-out abnormality. If in P39 the number of times of existence in the A layer is below the set value, that is, in the case that both the number of times of existence in the A layer and number of times of existence in difference places are below the set values, a decision is made to no abnormality (P39, P37).

iii) Detection of Evasion Action (a third monitoring operation, see FIGS. 9, 14, 4C)

Figure 4D:
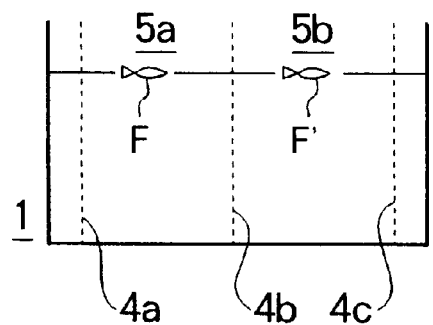

First, on the basis of the set parameters, continuous fourth layer existence frequency detecting means 54 checks whether or not the number of times of the fact that the fish F or F' under observation continuously stands in the fourth layer exceeds 3 (P51 in FIG. 14). If this number exceeds 3, a decision is made to that the evasion action starts, and hence it issues a command for the display of "confirmation of evasion action" to the display control means 46 (P52) so that the display control means 46 displays the "confirmation of evasion action" on the television scene 14a, with the result that the operation comes into the evasion action monitoring condition (P53). In response to the start of the monitoring operation, fourth layer existence frequency detecting means 55 and movement-to-different-place frequency detecting means 56 count the number of times of the fact the fish exists in the fourth layer for the monitoring time period and the number of times of the fact that the fish exists in places other than the fourth layer (P55, P56), and if the number of times of existence in different places within the monitoring time period exceeds a set value (3), an evasion action decision means 57 makes a decision to no abnormality even if the number of times of existence in the fourth layer exceeds a set value (3) (P56, P57) and further forwards a command for the deletion of the "confirmation of evasion action" to the display control means 46 (P58). Thus, the display "confirmation of evasion action" on the television scene 14a disappears. In the case that the number of times of movement to different places is below the set value (3) within the monitoring time period (2 minutes), after the elapse of the monitoring time period, it decides whether or not the number of times of existence in the fourth layer exceeds the set value (3) (P59). If exceeding the set value, in accordance with the decision to the evasion action, the first detection section 41a sends a first detection signal indicative of the evasion action to the alarm command means 44 while the second detection section 41b forwards a second detection signal indicative of the evasion action to the same alarm command means 44 (P61). In addition, it issues a command for the display of the "evasion abnormality" to the display control means 46 (P62), with the result that the display control means 46 permits the display "evasion abnormality" to appear on the television scene 14a. The delivery of the detection signals and the display command operation are continuously made during the detection of the evasion action. If in P59 the number of times of existence in the fourth layer is below the set value, that is, in cases where both the number of times of existence in different places and number of times of existence in the fourth layer are below the set values, a decision is made to no abnormality (P59, P57).

iv) Detection of Active State Abnormality (a fourth monitoring operation, see FIGS. 9, 15, 4D)

First, continuous stop time detecting means 58 detects whether or not a continuous stop time exceeds a set value (30 seconds) (P71 in FIG. 15). If this continuous stop time exceeds the set value, a decision is made to that the fish under observation stops to move, and hence the display control means 46 receives a display command for the display of "action stop" (P72), with the result that the operation comes into the active state abnormality monitoring condition (P73). Further, in accordance with the display command the display "action stop" appears on the television scene 14a. In response to the start of the monitoring operation, active state abnormality decision means 61 detects, through signal input frequency detecting means 59 and moving speed detecting means 60, whether or not the number of signal inputs exceeds a set value (5) for a monitoring time period (3 minutes) and whether or not the moving speed exceeds a set value (5 P/S) (P75, P76). If any one of these values exceeds the set value for the monitoring time period, a decision is made to no abnormality (P77), so that a command for the deletion of the display of "action stop" takes place (P78). Accordingly, the display of "action stop" on the television scene 14a disappears. In the case that both the number of signal inputs and the moving speed are below the set values even after the elapse of the monitoring time period, the death of the fish is decided (P79), so that the first detection section 41a sends a first detection signal indicative of the active state abnormality to the alarm command means 44 while the second detection section 41b forwards a second detection signal indicative of the active state abnormality to the same alarm command means 44 (P80). Further, a command for the display of "death abnormality" is issued to the display control means 46 (P81) so that the display "death abnormality" appears on the television scene 14*a*. The delivery of detection signals and the display command operation continue during the detection of the active state abnormality.

Figure 4E:
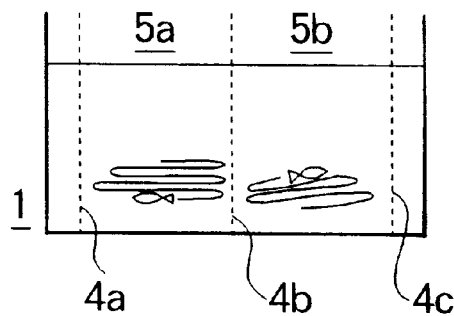

On the other hand, in cases where the fish F or F' under observation is in the normal condition, that is, when the fish under observation is normal as shown in FIG. 4E, since not taking any abnormal action pattern, the first or second detection section 41*a* or 41*b* does not detect the abnormal action pattern and does not output the detection signal to the alarm command means 44. In addition, if both the fish F, F' under observation show different abnormal action patterns, for example the first detection section 41*a* issues the first detection signal indicative of the upward putting-out action whereas the second detection section 41*b* generates the second detection signal representative of the evasion action.

Figure 4F:
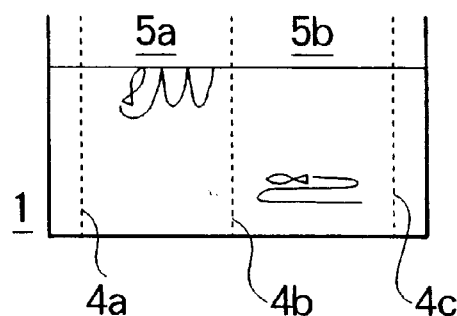

As described above, the alarm command means 44 continuously accepts the first or second detection signal as long as the abnormal action pattern takes place in any one of the monitoring sections 5*a*, 5*b*, and only when concurrently receiving the first and second detection signals indicative of the abnormal action patterns, that is, only when both the fish F, F' under observation in the first and second monitoring sections 5*a*, 5*b* assume some abnormal action pattern, an alarm command signal goes to the alarm driving means 45 (P6, P7 in FIG. 11). In other words, also in the case that the two fish under observation take different abnormal action patterns, the alarm works. Accordingly, in cases where only one detection signal is inputted into the aforesaid command means 44, for example if as shown in FIG. 4F the upward putting-out action is taken in only the first monitoring section 5*a* to cause the first detection section 41*a* to input the first detection signal while the fish F' under observation in the second monitoring section 5*b* is in the normal condition so that the second detection section 41*b* does not output the second detection signal, the output of the alarm command signal does not take place. The alarm driving means 45 operates the alarm 36 on the basis of the input of such command signals. An alarm buzzer, an alarm lamp and others constituting the alarm 36 are driven to raise an alarm indicative of the occurrence of the water quality abnormality. Besides, the alarm driving means 45 forwards a red lamp output signal so that the display control means 46 causes a red lamp to go on on the television scene 14*a*, thus expressing a warning representative of the occurrence of the water quality abnormality.

Although in the description of this embodiment the two monitoring sections are provided in the monitoring water tank 1, it is also appropriate that two or more monitoring sections are provided therein. In this instance, only when any abnormal action pattern is detected in all the monitoring section, the alarm operation is conducted. As the number of monitoring sections increases, the abnormality detection accuracy more improves. In addition, the most simplified construction is that one monitoring section is provided in the monitoring water tank 1, and even in this instance, a plurality of abnormal action patterns are detectable through the first to fourth monitoring operations in accordance with the above-described procedures, and if the alarm operation is conducted in response to the detection of any abnormal action pattern, more certain and accurate monitoring operation is possible as compared with the prior apparatus.

As described above, according to this embodiment, since the sensor points SP1, SP2 and others can freely set on the monitor television scene 14*a* corresponding to the image of the monitoring water tank 1, it is possible to avoid the detection of the luminance level variation at portions unnecessary for the image comparison but to detect only the luminance level variation in the necessary range on the television scene 14*a*, so that accurate and quick processing is realizable, and it is possible to cover the monitoring water tank with various shapes and sizes and further to enhance the degree of freedom on the installation of the monitoring water tank 1 and the video camera 12. In addition, with the preliminary decision based upon the parameters such as the madly running start speed for the detection of the madly running action, the number of times of continuous existence in the A layer for the detection of the upward putting-out action, the number of times of continuous existence in the fourth layer for the detection of the evasion action and the continuous stop time for the detection of the action abnormality, the district monitoring operation does not start until the pattern close to each of the abnormal action patterns develops, and therefore, even if the action pattern close to the abnormal action pattern appears, the following severer monitoring operation can decide that it is not an abnormal action pattern, with the result that more certain and accurate monitoring operation is practicable.

Furthermore, also in the monitoring operation conducted for the monitoring time period, the decision is made on the basis of the parameters such as the number of passing points for the detection of the madly running action, the number of times of movement to places other than the A layer for the detection of the upward putting-out action, the number of times of movement to places other than the fourth layer for the detection of the evasion action and the number of times of signal inputs and the moving speed for the detection of the active state abnormality, and hence the respective parameters can be set to agree with the natures of the aquatic living things to be raised, with the result that accurate and sure water quality monitoring operation is possible under the conditions most suitable for the characteristics of the aquatic living things. Further, since it is possible to freely set the monitoring time period so that the abnormal action patterns of the fish under observation are detectable in a state with being limited to the actions within the set time period, and hence the monitoring time period can be set in accordance with the nature of the fish under observation, which allows detecting the abnormal action pattern with a higher accuracy.

Moreover, for the detection of the upward putting-out action and the evasion action, the coordinate of the A layer near the water surface and the coordinate of the fourth layer close to the current plate can arbitrarily set to match with the size and nature of the fish or the like to be monitored, so that more accurate water quality monitoring operation is possible. In addition, since the abnormal action patterns are detected on the basis of the number of times of existence in the A layer and the fourth layer and the number of times of existence in places other than these layers, for example even if the number of times of existence in the A layer for the monitoring time period exceeds the set value, in the case that the number of times of existence in the different places also exceeds the set value, a decision can be made such that it is not the upward putting-out action but it is an action for having bait or like action, and therefore, even if a pattern close to the abnormal action pattern arises, it is possible to avoid the mistaken detection.

Still further, since the construction is made to monitor the fish F and F' under observation in the first and second monitoring sections 5*a*, 5*b*, even if for example one fish F takes an action close to the abnormal action pattern due to sickness or the like, in the case that the other fish F is normal, a decision is made to no occurrence of the water quality abnormality, and hence more precise water quality monitoring operation is practicable without depending upon the health condition of the fish under observation. In addition, since the monitoring water tank 1 is provided to be separated from the water receiving tank 8, it is not necessary that an aeration pump or the like is attached to the monitoring water tank 1 and hence the bubbles produced by the same pump do not directly enter the monitoring water tank 1, which can prevent the malfunction due to the bubbles and others at detection. Further, since the raw water receiving section 4a' is provided in the current plate 4a of the monitoring water tank 1, it is possible to prevent the bubbles, dust and others from entering the monitoring sections 5a, 5b. Besides, since the gap t is defined between the current plate of the monitoring water tank 1 and the inner lower surface of the same water tank 1, it is possible to discharge the dust, duckweed and others, produced in the monitoring water tank 1, through the same gap section and hence to prevent the dust and others from staying within the monitoring water tank 1.

As described above, according to this invention, since a plurality of sensor points can freely be set on the monitor television scene corresponding to the image of the monitoring water tank, it is possible to detect only the luminance level variation in the necessary range on the television scene without detecting the luminance level variation in the portion unnecessary for the image comparison so that accurate and quick processing is realizable, and further the operation can be made to agree with the monitoring water tank with various shapes and dimensions and the degree of freedom on the location of the monitoring water tank and the television camera can increase. In addition, for the detection of the abnormal action patterns, a decision is made by comparing the position data successively inputted with various parameters within the set monitoring time period, and therefore the monitoring time period and the respective parameters can be set in accordance with the characteristics of the aquatic living things to be raised, with the result that an accurate and certain water quality monitoring operation is possible under the condition most suitable for the nature of the aquatic living things.

Furthermore, in the second or third monitoring operation, the position of the first layer in the vicinity of the water surface or the position of the second layer on the water discharge outlet side can be set to agree with the sizes, characteristics and others of the aquatic living things under monitoring, which can ensure a more accurate water quality monitoring operation. In addition, the detection of the abnormal action patterns is made on the basis of the number of times of existence in the first or second layer and the number of times of existence in places other than these layers, irrespective of a pattern close to the abnormal action pattern the mistaken detection is avoidable and an accurate monitoring operation is realizable. Further, the first to fourth abnormal action patterns are detectable through the first to fourth monitoring operations and the alarm is issued in response to the detection of any one of the abnormal action patterns, and therefore the water quality abnormality is detectable on the basis of a plurality of abnormal action patterns of the aquatic living things, which can realize a more certain water quality monitoring operation. Moreover, since the fish under observation are monitored in a plurality of monitoring sections and the alarm is raised in response to only the detection of the abnormal action patterns in all the monitoring sections, even if, for example, only one fish shows an abnormal action pattern, in the case that the action patterns of the other fish are in the normal conditions, a decision can be made to that that problem is concerned with only that fish, with the result that a more accurate water quality monitoring operation is possible without depending upon the health condition of the fish under observation or the like.

It should be understood that the foregoing relates to only a preferred embodiment of the present invention, and that it is intended to cover all changes and modifications of the embodiment of the invention herein used for the purposes of the disclosure, which do not constitute departures from the spirit and scope of the invention.

What is claimed is:

1. A water quality monitoring apparatus using an aquatic living thing, comprising:

a monitoring water tank for accommodating raw water to raise said aquatic living thing in said raw water;

a monitoring camera for photographing said aquatic living thing within said monitoring water tank;

a monitor television for displaying an image taken through said monitoring camera;

point setting means for setting a plurality of sensor points in said image of said monitoring water tank displayed on said monitor television;

sensing means for recognizing a position of each of said sensor points, and for detecting the occurrence or no occurrence of variation of each of said sensor points in luminance level due to movement of said aquatic living thing at a given time interval, and further for, when detecting the luminance level variation, outputting position data corresponding to the position of the luminance level varied sensor point;

abnormal action pattern detecting means for monitoring an action pattern of said aquatic living thing on the basis of said position data outputted from said sensing means for a set monitoring period of time and for deciding whether or not said action pattern taken for said monitoring time period is an abnormal action pattern; and alarm means for raising an alarm in accordance with a decision result produced by said abnormal action pattern detecting means.

2. An apparatus as defined in claim 1, wherein said abnormal action pattern detecting means calculates a moving distance of said aquatic living thing for said monitoring time period on the basis of the said position data outputted from said sensing means and makes a decision to said abnormal pattern when the calculated moving distance exceeds a set distance while making a decision to no abnormality when being below said set value.

3. An apparatus as defined in claim 1, wherein said point setting means determines as a first layer a layer with a given depth right under a water surface in said monitoring water tank, said first layer extending in a horizontal direction within said image of said monitoring water tank displayed on said monitor television, and sets said plurality of sensor points inside and outside said first layer, and said abnormal action pattern detecting means counts, on the basis of said position data outputted from said sensing means, a first number of times of output of said position data indicative of said sensor points within said first layer for said monitoring time period and a second number of times of output of said position data representative of said sensor points outside said first layer for said monitoring time period, and makes a decision to no abnormality when the second number of times of output exceeds a second set value while making a decision of the occurrence of said abnormal action pattern when the first number of times of output exceeds a first set value and the second number of times of output is below said second set value.

4. An apparatus as defined in claim 1, wherein said point setting means determines as a second layer a layer with a given width, extending in a vertical direction in the vicinity of a water discharge outlet within an image of said monitoring water tank displayed on said monitor television, and sets said plurality of sensor points inside and outside said second layer, and said abnormal action pattern detecting means counts, on the basis of said position data outputted from said sensing means, a third number of times of output of said position data indicative of said sensor points within said second layer within said monitoring time period and a fourth number of times of output of said position data representative of said sensor points outside said second layer, and makes a decision to no abnormality when the fourth number of times of output exceeds a fourth set value whereas making a decision to the occurrence of said abnormal action pattern if the third number of times of output exceeds a third set value and the fourth number of times of output is still below said fourth set value.

5. An apparatus as defined in claim 1, wherein on the basis of said position data outputted from said sensing means said abnormal action pattern detecting means counts the number of times of output of said position data for said monitoring time period and calculates a moving speed of said aquatic living thing and makes a decision to no abnormality when the number of times of output exceeds a set value or the calculated moving speed exceeds a set value while making a decision to the occurrence of said abnormal action pattern if the number of times of output is below said set value and the calculated moving speed is lower than said set value.

6. An apparatus as defined in claim 1, wherein said monitoring water tank is divided into a plurality of monitoring sections each for raising said aquatic living thing, and said point setting means sets a plurality of sensor points in each of said monitoring sections, and said sensing means detects the occurrence or no occurrence of the luminance level variation of each of said sensor points at given time interval and, when detecting the occurrence of the luminance level variation, outputs position data corresponding to the position of said sensor point where the luminance level variation occurs, and further said abnormal action pattern detecting means monitors an action pattern of said aquatic living thing in each of said monitoring sections so that said alarm means issues an alarm only when a decision is made to that the action patterns of the aquatic living things are the abnormal action patterns in all said monitoring sections.

* * * * *